US008580945B2

(12) United States Patent
Prchal et al.

(10) Patent No.: US 8,580,945 B2
(45) Date of Patent: Nov. 12, 2013

(54) OLIGONUCLEOTIDES FOR USE IN ALLELE-SPECIFIC PCR

(75) Inventors: Josef T. Prchal, Salt Lake City, UT (US); Roberto H. Nussenzveig, South Jordan, UT (US); Sabina I. Swierczek, West Jordan, UT (US)

(73) Assignee: University of Utah, Salt Lake City, UT (US)

( * ) Notice: Subject to any disclaimer, the term of this patent is extended or adjusted under 35 U.S.C. 154(b) by 909 days.

(21) Appl. No.: 12/513,467

(22) PCT Filed: Nov. 2, 2007

(86) PCT No.: PCT/US2007/083456
§ 371 (c)(1),
(2), (4) Date: Nov. 23, 2009

(87) PCT Pub. No.: WO2008/070370
PCT Pub. Date: Jun. 12, 2008

(65) Prior Publication Data
US 2010/0068712 A1    Mar. 18, 2010

Related U.S. Application Data

(60) Provisional application No. 60/864,099, filed on Nov. 2, 2006.

(51) Int. Cl.
C07H 21/04 (2006.01)
C12Q 1/68 (2006.01)
C12P 19/34 (2006.01)

(52) U.S. Cl.
USPC ................ 536/24.33; 435/6.12; 435/91.2

(58) Field of Classification Search
None
See application file for complete search history.

(56) References Cited

U.S. PATENT DOCUMENTS

2007/0224598 A1 *  9/2007  Chang ............................. 435/6

FOREIGN PATENT DOCUMENTS

| EP | 332435 A2 * | 9/1989 |
| EP | 1 247 815 A2 | 10/2002 |
| WO | WO 00/56916 A2 | 9/2000 |
| WO | WO 02/097109 A2 | 12/2002 |
| WO | WO 03/018835 A2 | 3/2003 |
| WO | WO 03/072814 A2 | 9/2003 |
| WO | WO 2004/020575 A2 | 3/2004 |

OTHER PUBLICATIONS

Chen et al. Cancer Epidemiology, Biomarkers & Prevention (2002) 11: 131-136.*
Kutyavin, Igor V., et al., "Oligonucleotides Containing 2-Aminoadenine and 2-Thiothymine Act as Selectively Binding Complementary Agents," 35(34) *Biochemistry* 11170-11176 (1996).
Orum, Henrik, et al., "Detection of the Factor V Leiden Mutation by Direct Allele-specific Hybridization of PCR Amplicons to Photoimmobilized Locked Nucleic Acids," 45(11) *Clinical Chemistry* 1898-1905 (1999).
European Patent Office Communication and Supplementary European Search Report for European Application No. 07871341.9, 6 pages (Jul. 7, 2010).
Examination Report from related EP Application No. 07871341.9, dated Jun. 27, 2011 (8 pages).
Johnson, MP, et al, "Locked Nucleic Acid (LNA) Single Nucleotide Polymorphism (SNP) Genotype Analysis and Validation Using Real-Time PCR", *Nucleic Acids Research*, Oxford University Press, Surrey, GB, vol. 32, No. 6, 9 pages (Mar. 26, 2004).
Song, Pengfei et al., "Detection of MDR1 single nucleotide polymorphisms C3435T and G2677T using real-time polymerase chain reaction: MDR1 single nucleotide polymorphism genotyping assay," *AAPS PHARMSCI* 2002 LNKD—PUBMED:12646001, vol. 4, No. 4, 6 pages (2002).
Ahmadian, Afshin, et al., "Genotyping by apyrase-mediated allele-specific extension," *Nucleic Acids Research*, 29(24):e-121, pp. 1-5 (2001).
Baxter, E. Joanna, et al., "Acquired mutation of the tyrosine kinase JAK2 in human myeloproliferative disorders," *Lancet*, 365:1054-61 (Mar. 19, 2005).
Bellané-Chantelot, Christine, et al., "Genetic and clinical implications of the Val617Phe JAK2 mutation in 72 families with myeloproliferative disorders," *Blood*, 108(1):346-352 (Jul. 1, 2006).
Bottema, Cynthia D.K., et al., "PCR amplification of specific alleles: Rapid detection of known mutations and polymorphisms," *Mutation Research*, 288:93-102 (1993).
Germer, Søren, et al., "High-Throughput SNP Allele-Frequency Determination in Pooled DNA Samples by Kinetic PCR," *Genome Res.*, 10:258-266 (2000).
James, Chloé, et al., "A unique clonal *JAK2* mutation leading to constitutive signaling causes polycythaemia vera," *Nature*, 434:1144-1148 (Apr. 28, 2005).
Jelinek, Jaroslav, et al., "JAK2 mutation 1849G>T is rare in acute leukemias but can be found in CMML, Philadelphia chromosome-negative CML, and megakaryocytic leukemia," *Blood*, 106(10):3370-3373 (Nov. 15, 2005).
Jelinek, Jaroslav, et al., "Oxygen-Dependent Regulation of Erythropoiesis," *Methods of Enzymology*, 381:201-210 (2004).
Kaltenböck, Bernhard, et al., "Differential Amplification Kinetics for Point Mutation Analysis by PCR," *BioTechniques*, 24(2):202-206 (Feb. 1998).
Kralovics, Robert, et al., "Clonal hematopoiesis in familial polycythemia vera suggests the involvement of multiple mutational events in the early pathogenesis of the disease," *Blood*, 102(10):3793-3796 (Nov. 15, 2003).

(Continued)

*Primary Examiner* — Angela M Bertagna
(74) *Attorney, Agent, or Firm* — Brinks Gilson & Lione; Ryan L. Marshall

(57) ABSTRACT

The present invention relates to oligonucleotides complementary to a target polynucleotide, wherein the oligonucleotide comprises an LNA unit, a mismatch nucleobase, and an allele-specific nucleobase corresponding to an allele of the target polynucleotide. The invention further includes methods of using such oligonucleotides to detect and quantitate the frequency of particular alleles of a target polynucleotide.

19 Claims, 4 Drawing Sheets

(56) References Cited

OTHER PUBLICATIONS

Kralovics, Robert, et al., "Acquired uniparental disomy of chromosome 9p is frequent stem cell defect in polycythemia vera," *Experimental Hematology*, 30:229-236 (2002).

Kralovics, Robert, et al., "A Gain-of-Function Mutation of *JAK2* in Myeloproliferative Disorders,"*N. Engl. J. Med.*, 352(17):1779-1790 (Apr. 28, 2005).

Lacout, Catherine, et al., "JAK2V617F expression in murine hematopoietic cells leads to MPD mimicking human PV with secondary myelofibrosis," Blood, 108(5):1652-1660 (Sep. 1, 2006).

Latorra, David, et al., "Enhanced Allele-Specific PCR Discrmination in SNP Genotyping Using 3' Locked Nucleic Acid (LNA) Primers," *Human Mutation*, 22:79-85 (2003).

Latorra, David, et al., "Design considerations and effects of LNA in PCR primers," *Molecular and Cellular Probes*, 17:253-259 (2003).

Levine, Ross L., et al., "Activating mutation in the tyrosine kinase JAK2 in polycythemia vera, essential thrombocythemia, and myeloid metaplasia with myelofibrosis," *Cancer Cell*, 7:387-397 (Apr. 2005).

Liu, Enli, et al., "Discrimination of polycythemias and thrombocytoses by novel, simple, accurate clonality assays and comparison with PRV-1 expression and BFU-E response to erythropoietin," *Blood*, 101(8):3294-3301 (Apr. 15, 2003).

Newton, C.R., et al., "Analysis of any point mutation in DNA. The amplification refractory mutation system (ARMS)," *Nucleic Acids Research*, 17(7):2503-2516 (1989).

Petersen, Michael, et al., "The conformations of locked nucleic acids (LNA)," *J. Mol. Recognit.*, 13:44-53 (2000).

Prchal, Josef T., "Polycythemia vera and other primary polycythemias," *Curr. Opin. Hematol.*, 12:112-116 (2005).

Prchal, Jaroslav F., et al., "Human Erythroid Colony Formation In Vitro: Evidence for Clonal Origin," *J. Cell. Physiol.*, 89:489-492 (1976).

Prchal, J. F., et al., "Bone-Marrow Responses in Polycythemia Vera," *The New England Journal of Medicine*, p. 1382 (Jun. 13, 1974).

Scott, Linda M., et al., "Progenitors homozygous for the V617F mutation occur in most patients with polycythemia vera, but not essential thrombocythemia," *Blood*, 108(7):2435-2437 (Oct. 1, 2006).

Skoda, Radek, et al., "Chronic Myeloproliferative Disorders—Introduction," *Seminars in Hematology* 42(4):181-183 (Oct. 2005).

Stopka, T., et al., "Human Hematopoietic Progenitors Express Erythropoietin," *Blood*, 91(10):3766-3772 (May 15, 1998).

Ugo, Valérie, et al., "Multiple signaling pathways are involved in erythropoietin-independent differentiation of erythroid progenitors in polycythemia vera," *Experimental Hematology*, 32:179-187 (2004).

Zhao, Runxiang, et al., "Identification of an Acquired JAK2 Mutation in Polycythemia Vera," *The Journal of Biological Chemistry*, 280(24): 22788-22792 (Jun. 17, 2005).

\* cited by examiner

OLIGONUCLEOTIDES FOR USE IN ALLELE-SPECIFIC PCR

REFERENCE TO EARLIER FILED APPLICATION

This application is a 371 national phase of PCT/US2007/083456, filed Nov. 2, 2007, and claims the benefit under 35 U.S.C. §119(e) of U.S. Provisional Patent Application No. 60/864,099, filed Nov. 2, 2006, the disclosures of which are incorporated, in their entirety, by this reference.

TECHNICAL FIELD OF THE INVENTION

The present invention relates to novel oligonucleotides for use in allele-specific PCR.

BACKGROUND OF THE INVENTION

A variety of methods are currently employed in molecular biology and clinical diagnostic to identify polymorphisms (e.g., single nucleotide polymorphisms (SNPs) and mutations) in DNA or RNA. Such methods include kinetic PCR, microarrays, RNA interference, antisense inhibition or nanosensors. Discrimination between polymorphic variations typically relies upon detection systems based on melting temperature differences between perfectly matched and mismatched duplexes relative to a hybridizing probe. The utility of such hybridization-based methods, however, is limited because the differences in melting temperature are typically too small to discriminate single mismatches within probes. Although shorter probes can be used to improve detection of a mismatch, they sacrifice specificity for discrimination when used in complex nucleic acid samples.

Recently, chimeric probes having select positions modified with locked nucleic acids (LNAs) have been reported to enhance both duplex stability and mismatch discrimination. LNA monomers contain a modified ribose moiety and are somewhat similar to 2'-O-methyl RNA, except that the O-methyl group bridges and constrains the 2' and 4' carbons of the ribose ring. This covalent bridge effectively 'locks' the ribose in the N-type (3'-endo) conformation that is dominant in A-form DNA and RNA. This locked conformation enhances base stacking and phosphate backbone pre-organization and significantly increases the thermal stability of the oligonucleotide, resulting in improved affinity for complementary DNA or RNA sequences (higher $T_m$).

The enhanced affinity of LNA nucleotides increases the sensitivity and specificity of expression analysis in cDNA microarrays, FISH probes, real-time PCR probes and other molecular biology techniques based on oligonucleotide hybridization. For example, chimeric oligonucleotides incorporating LNA units have been shown to be useful for allele-specific PCR detection of polymorphisms. Johnson et al. (Nucleic Acids Research, 2004, Vol. 32, No. 6 e55) disclose LNA oligonucleotides for allele-specific PCR (AS-PCR), with LNA added throughout at several positions in the primer. Chou et al. (BioTechniques 39:644-650 (November 2005)) disclose LNA oligos with the LNA at the −5 position. Latorra et al., Human Mutation 22:79-85 (2003) and Latorra et al., BioTechniques 34:1150-1158 (June 2003), also disclose LNA oligos with the LNA at the 3' end of the primer. You et al., Nucleic Acids Research, 2006, Vol. 34, No. 8 e60, disclose LNA oligonucleotides for detecting SNPs based on melting curve analysis. Incorporating deliberate mismatches into primers for AS-PCR is another technique which has been used to improve discrimination. For example, Song et al., AAPS PharmSci 2002; 4 (4) article 29, designed primers that incorporate a deliberate mismatch at the −3 position.

The present invention is directed to oligonucleotides that demonstrate improved ability to discriminate between alleles on the basis of single nucleotide polymorphisms.

SUMMARY OF THE INVENTION

The present invention is generally directed to oligonucleotides that incorporate a locked nucleic acid (LNA) and a mismatch nucleic acid.

In one aspect, the present invention includes oligonucleotides complementary to a target polynucleotide, wherein the oligonucleotide comprises an LNA unit, a mismatch nucleobase, and an allele-specific nucleobase corresponding to an allele of the target polynucleotide.

In another aspect, the present invention includes a duplex comprising an oligonucleotide hybridized to a target polynucleotide, wherein the oligonucleotide is complementary to the target polynucleotide and comprises an LNA unit, a mismatch nucleobase and an allele-specific nucleobase corresponding to an allele of the target polynucleotide.

In another aspect, the present invention includes a method of detecting the presence or absence of a target polynucleotide in a biological sample, comprising:

(a) providing an oligonucleotide complementary to a target polynucleotide, wherein the oligonucleotide comprises an LNA unit, a mismatch nucleobase, and an allele-specific nucleobase corresponding to an allele of the target polynucleotide;

(b) combining the oligonucleotide of (a) with a biological sample suspected of containing the target polynucleotide;

(c) detecting the presence or absence of hybridization and extension of the oligonucleotide with the target polynucleotide, wherein hybridization and extension of the oligonucleotide with the target polynucleotide is indicative of the presence of an allele corresponding to the allele-specific nucleobase.

In another aspect, the present invention includes a method of detecting the presence or absence of a polymorphism in a target nucleotide in a biological sample, comprising:

(a) providing an oligonucleotide primer complementary to a target polynucleotide, wherein the oligonucleotide primer comprises an LNA unit, a mismatch nucleobase, and an allele-specific nucleobase corresponding to an allele of the target polynucleotide;

(b) combining the oligonucleotide primer of (a) and a polymerase enzyme with a biological sample suspected of containing a target polynucleotide under conditions amenable to hybridization of the oligonucleotide primer with the target polynucleotide and synthesis of a primer extension product;

(c) detecting the presence or absence of a primer extension product, wherein the presence of a primer extension product is indicative of the presence of an allele corresponding to the allele-specific nucleobase.

In yet another aspect, the present invention includes a method of quantitatively determining the frequency of a first allele and a second allele of a target polynucleotide in a biological sample, comprising:

(a) amplifying a target polynucleotide in a biological sample using a first oligonucleotide complementary to a first allele of the target polynucleotide, wherein the first oligonucleotide comprises an LNA unit, a mismatch nucleobase, and an allele-specific nucleobase corresponding to a first allele of the target polynucleotide;

(b) amplifying a target polynucleotide in a biological sample using a second oligonucleotide complementary to a second allele of the target polynucleotide, wherein the second oligonucleotide comprises an LNA unit, a mismatch nucleobase, and an allele-specific nucleobase corresponding to a second allele of the target polynucleotide;

(c) comparing the cycle threshold for the amplification of (a) and (b);

(d) determining the frequency of the first allele and the second allele.

In another aspect, the present invention includes a method of quantitatively determining the frequency of an allele of a target polynucleotide in a biological sample, comprising:

(a) amplifying a target polynucleotide in a biological sample using a first oligonucleotide complementary to an allele of the target polynucleotide, wherein the first oligonucleotide comprises an LNA unit, a mismatch nucleobase, and an allele-specific nucleobase corresponding to a first allele of the target polynucleotide;

(b) calculating the cycle threshold for (a);

(c) comparing the cycle threshold for (a) with the cycle threshold for amplification of a known standard;

(d) determining the frequency of the allele.

In some embodiments of the invention, the LNA unit and the mismatch nucleobase are contiguous. In other embodiments, the mismatch nucleobase and the allele-specific nucleobase are contiguous. In other embodiments, the LNA unit, the mismatch nucleobase and the allele-specific nucleobase are contiguous.

In a particular embodiment of the invention, the LNA unit is at the −2 position relative to the allele-specific nucleobase. In another particular embodiment of the invention, the mismatch nucleobase is at the −1 position relative to the allele-specific nucleobase. In yet another particular embodiment, the LNA unit is at the −2 position and the mismatch nucleobase is at the −1 position relative to the allele-specific nucleobase.

In still another embodiment, the allele-specific nucleobase is at the 3' terminal position. In still another embodiment, the allele-specific nucleobase is at the 3' terminal position and the LNA unit is at the −2 position relative to the allele-specific nucleobase. In another particular embodiment, the allele-specific nucleobase is at the 3' terminal position and the mismatch nucleobase is at the −1 position relative to the allele-specific nucleobase.

In a more particular embodiment, the allele-specific nucleobase is at the 3' terminal position, the LNA unit is at the −2 position and the mismatch nucleobase is at the −1 position relative to the allele-specific nucleobase.

In some embodiments of the invention, the allele-specific nucleobase is complementary to the target polynucleotide. In other embodiments, the allele-specific nucleobase is non-complementary to the target polynucleotide.

In other embodiments of the invention, the oligonucleotide is a primer.

DETAILED DESCRIPTION OF THE INVENTION

Figure 1:
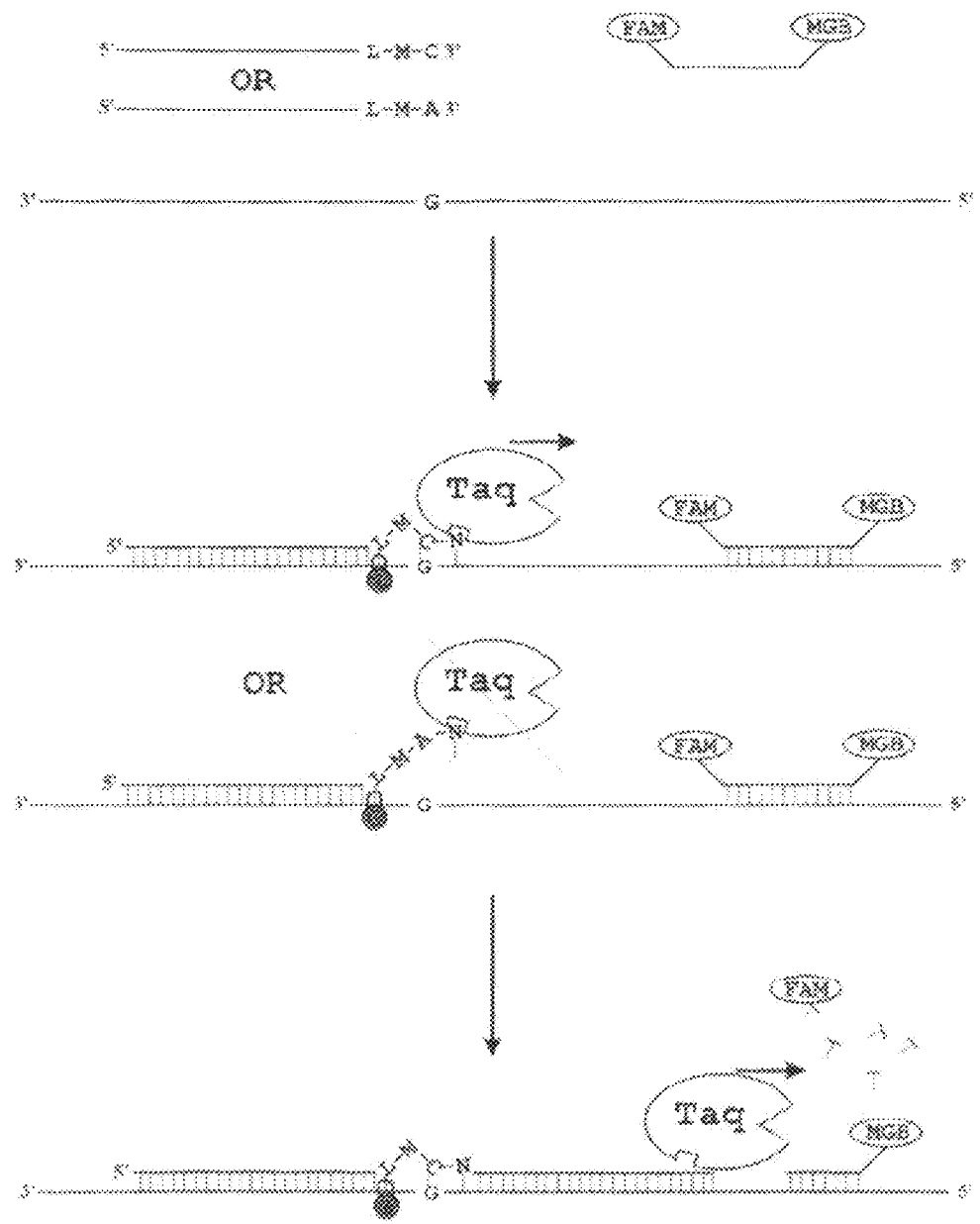
FIG. 1 is a diagram showing the mechanism of action of the primers of the present invention. The diagram depicts the strand used for allele-specific priming and extension. The strand primed and extended by the universal primer is not shown. In the first step, two different reactions are prepared, each containing one of the allele-specific primers and the universal primer. In the second step, after heat denaturation, the allele-specific primer anneals and, depending on stability of the 3' end hybridization, Taq DNA polymerase extension occurs. Finally, in the third step, once extension takes place, the 5' to 3' exonuclease activity of Taq cleaves the probe between the reporter and quencher. Subsequent PCR cycles favor the newly synthesized strand since it incorporates the mismatched nucleoside. While LNA, in our primer design, helps stabilize 3' end annealing and increase Tm, resulting in enhanced specificity and efficiency of the reaction.

Unless defined otherwise, technical and scientific terms used herein have the same meaning as commonly understood by one of ordinary skill in the art to which this invention pertains. Units, prefixes, and symbols may be denoted in their SI accepted form. Unless otherwise indicated, nucleic acids are written left to right in 5' to 3' orientation. Numeric ranges recited herein are inclusive of the numbers defining the range and include and are supportive of each integer within the defined range. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes. Unless otherwise noted, the terms "a" or "an" are to be construed as meaning "at least one of." The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. In the case of any amino acid or nucleic sequence discrepancy within the application, the figures control. One skilled in the art will recognize many methods and materials similar or equivalent to those described herein, which could be used in the practice of the present invention. The present invention is in no way limited to the methods and materials described herein, and it is understood that other embodiments of the invention may exist that are not expressly described herein. For purposes of the present invention, the following terms are defined below.

The term "allele," as used herein, means a particular genetic variant or polymorphism in the sequence of a gene, representing an alternative form of the gene.

The term "target polynucleotide," as used herein, refers to a region of a polynucleotide template sequence that is to be detected and amplified. The target polynucleotide may represent a wild-type or consensus sequence, a characteristic of the predominant form of the gene, or alternatively may represent a polymorphic variant that is present in a population at a lower frequency.

The term "allele-specific," when used in reference to nucleic acid sequences, such as oligonucleotides and primers, means that a particular position of the nucleic acid sequence is complementary with an allele of a target polynucleotide sequence. Allele-specific primers are capable of discriminating between different alleles of a target polynucleotide. While the allele-specific nucleobase of the oligonucleotides of the invention are preferably complementary to one allele of a target polynucleotide sequence, it is also contemplated that the "allele-specific" nucleobase may not be exactly complementary to any allele of the target polynucleotide. It is further understood that the oligonucleotides of the invention includes deliberate mismatches (at a different position than the allele-specific nucleobase) such that the oligonucleotide is not exactly complementary to the target polynucleotide. The function of the allele-specific oligonucleotides of the present invention is to facilitate preferential hybridization and extension under PCR conditions of primers having the allele-specific nucleobase, or, alternatively, suppressing hybridization and extension of primers not have the allele-specific nucleobase.

The terms "complementary" and "complement," when used in reference to two nucleic acid sequences, means that when two nucleic acid sequences are aligned in anti-parallel association (with the 5' end of one sequence paired with the 3' end of the other sequence) the corresponding G and C nucleotide bases of the sequences are paired, and the corresponding A and T nucleotide bases are paired. The term "complementary" is not limited to canonical Watson-Crick base pairs with A/T, G/C and U/A. Thus, nucleobase pairs may be considered to be complementary if one or both of the nucleobases is a nucleobase other than A, G, C, or T, such as a universal or degenerate nucleobase. For example, certain bases not commonly found in natural nucleic acids may be included in the nucleic acids of the present invention and include, for example, inosine and 7-deazaguanine. A degenerate or universal nucleobase that is complementary to two or more corresponding nucleobases is considered to hybridize non-selectively to the two or more corresponding nucleobases. The term "complementary" also refers to antiparallel strands of polynucleotides (as opposed to a single nucleobase pair) that are capable of hybridizing. The term "complementary," as used in reference to two nucleotide sequences or two nucleobases, implies that the nucleotides sequences or nucleobases are "corresponding."

The primers herein are selected to be substantially complementary to the different strands of each specific sequence to be amplified, such that the primers are sufficiently complementary to hybridize with their respective strands. Typically, the primers have exact complementarity to obtain the best detection results, but in accordance with the present invention mismatches are incorporated into the oligonucleotide primers so that the primers are substantially complementary to the template strand. The primer sequence need not, however, reflect the exact sequence of the template at positions other than the mismatch. For example, the oligonucleotide may include not only a mismatch nucleobase, but may also additional mismatches at other positions sufficiently remote from the LNA unit (for example, at the 5' end of the oligonucleotide), mismatch nucleobase and the allele-specific nucleobase that it would not interfere with the discriminatory function of the oligonucleotide.

The term "corresponding," when used to refer to two nucleotide sequences or two nucleobases within a sequence, means having the same or nearly the same relationship with respect to position and/or complementarity, or having the same or nearly the same relationship with respect to structure, function, or genetic coding (for example, as between a gene and the "corresponding" protein encoded by the gene). For example, a nucleotide sequence "corresponds" to a region of a polynucleotide template if the two sequences are complementary or have portions that are complementary. Similarly, a nucleobase of an oligomer "corresponds" to a nucleobase of a polynucleotide template when the two nucleobases occupy a position such that when the oligomer and the polynucleotide hybridize the two nucleobases pair opposite each other. The term "corresponding" is generally used herein in reference to the positional relationship between two polynucleotide sequences or two nucleobases. The term "corresponding" does not imply complementarity; thus, corresponding nucleobases may be complementary, or may be non-complementary.

The term "duplex" means a bimolecular nucleic acid complex, usually formed through association of a series of interacting nucleobase dyads, one from each molecule of the complex. A single nucleic acid molecule may also have regions of duplex association by folding back onto itself and intramolecularly hybridizing to a complementary sequence.

The term "locked nucleic acid" or "LNA" means a synthetic nucleic acid analogue, incorporating "internally bridged" nucleoside analogues, for example, 2'-4'- and 3'-4'-linked and other bicyclic sugar modifications. LNA exhibits greater thermal stability when paired with DNA, than do conventional DNA/DNA heteroduplexes and can be synthesized on conventional nucleic acid synthesizing machines. LNA molecules, and methods of synthesizing and using LNA molecules in oligonucleotide, are well-known in the art and are disclosed, for example, in the following publications: U.S. Pat. Nos. 6,316,198; 6,794,499; 7,034,133; 7,060,809; and 7,034,133; WO 98/22489; WO 98/39352; WO 99/14226; Nielsen et al., *J. Chem. Soc. Perkin Trans.* 1, 3423 (1997); Koshkin et al., *Tetrahedron Letters* 39, 4381 (1998); Singh & Wengel, *Chem. Commun,* 1247 (1998); and Singh et al., *Chem. Commun.* 455 (1998); the contents of which are incorporated herein by reference in their entirety.

The term "mismatch nucleobase," as used herein, means a natural nucleobase that is not complementary to the corresponding nucleobase of the opposite polynucleotide strand. The term "mismatch nucleobase" excludes LNA units, which are not natural nucleobases.

The term "nucleic acid" as used herein means a nucleobase polymer having a backbone formed from nucleotides, or nucleotide analogs. "Nucleic acid" and "polynucleotide" are considered to be equivalent and interchangeable, and refer to polymers of nucleic acid bases comprising any of a group of complex compounds composed of purines, pyrimidines, carbohydrates, and phosphoric acid. Nucleic acids are commonly in the form of DNA or RNA. The term "nucleic acid" includes polynucleotides of genomic DNA or RNA, cDNA, semi-synthetic, or synthetic origin. Nucleic acids may also substitute standard nucleotide bases with nucleotide isoform analogs, including, but not limited to iso-C and iso-G bases, which may hybridize more or less permissibly than standard bases, and which will preferentially hybridize with complementary isoform analog bases. In representations of degenerate primers or mixture of different strands having mutations in one or several positions, the symbol R refers to either G or A, the symbol Y refers to either T/U or C, the symbol M refers to either A or C, the symbol K refers to either G or T/U, the symbol S refers to G or C, the symbol W refers to either A or T/U, the symbol B refers to "not A", the symbol D refers to "not C", the symbol H refers to "not G", the symbol V refers to "not T/U" and the symbol N refers to any nucleotide.

As used herein, the term "nucleic acid polymerase" refers to an enzyme which catalyzes the polymerization of nucleoside triphosphates to form the primer extension products which are complementary to each nucleic acid strand. Polymerase enzymes initiate synthesis at the 3'-end of the primer annealed to the target sequence, and will proceed in the 5' to 3' direction along the template strand, until synthesis terminates, producing an extension product. Suitable nucleic acid polymerase enzymes for use in the present invention lack 3' to 5' exonuclease activity (also known as proofreading) and are well-known to those skilled in the art.

The term "nucleobase" as used herein means any nitrogen-containing heterocyclic moiety capable of forming Watson-Crick-type hydrogen bonds and stacking interactions in pairing with a complementary nucleobase or nucleobase analog (i.e., derivatives of nucleobases) when that nucleobase is incorporated into a polymeric structure. "Heterocyclic" refers to a molecule with a ring system in which one or more ring atom is a heteroatom, e.g., nitrogen, oxygen, or sulfur (i.e., not carbon), such as a purine, pyrimidine, or analog thereof.

A large number of nucleobases, nucleobase analogs and nucleobase derivatives are known. Non-limiting examples of nucleobases include purines and pyrimidines, and modified forms, e.g., 7-deazapurine. Typical nucleobases are the naturally occurring nucleobases adenine, guanine, cytosine, uracil, thymine, and analogs (Seela, U.S. Pat. No. 5,446,139) of the naturally occurring nucleobases, e.g., 7-deazaadenine, 7-deazaguanine, 7-deaza-8-azaguanine, 7-deaza-8-azaadenine, inosine, nebularine, nitropyrrole (Bergstrom, J. Amer. Chem. Soc., 117:1201-1209 [1995]), nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine (Seela, U.S. Pat. No. 6,147,199), 7-deazaguanine (Seela, U.S. Pat. No. 5,990,303), 2-azapurine (Seela, WO 01/16149), 2-thiopyrimidine, 6-thioguanine, 4-thiothymine, 4-thiouracil, O.sup.6-methylguanine, N.sup.6-methyladenine, O.sup.4-methylthymine, 5,6-dihydrothymine, 5,6-dihydrouracil, 4-methylindole, pyrazolo[3,4-D]pyrimidines, "PPG" (Meyer, U.S. Pat. Nos. 6,143,877 and 6,127,121; Gall, WO 01/38584), and ethenoadenine (Fasman (1989) in Practical Handbook of Biochemistry and Molecular Biology, pp. 385-394, CRC Press, Boca Raton, Fla.).

The term "nucleoside" as used herein means a nucleobase linked to a carbohydrate. Nucleosides are coupled to D-ribose (in RNA) or 2'-deoxy-D-ribose (in DNA) carbohydrate through an N-glycosidic bond between the anomeric carbon of the carbohydrate (1'-carbon atom of the carbohydrate) and the N9 of a purine or N1 of a pyrimidine. When the nucleobase is purine, e.g., A or G, the ribose sugar is attached to the N9-position of the nucleobase. When the nucleobase is pyrimidine, e.g., C, T or U, the sugar is attached to the N'-position of the nucleobase. The carbohydrate may be substituted or unsubstituted. Substituted ribose sugars include, but are not limited to, those in which one or more of the carbon atoms, for example the 2'-carbon atom, is substituted with one or more of the same or different Cl, F, —R, —OR, —NR$_2$ or halogen groups, where each R is independently H, C1-C6 alkyl or C5-C14 aryl. Ribose examples include ribose, 2'-deoxyribose, 2',3'-dideoxyribose, 2'-haloribose, 2'-fluororibose, 2'-chlororibose, and 2'-alkylribose, e.g., 2'-O-methyl, 4'-alpha-anomeric nucleotides, and 1'-alpha-anomeric nucleotides (Asseline et al., Nucl. Acids Res., 19:4067-74 [1991]).

Carbohydrates (also called sugars) can include modifications at the 2'- or 3'-position such as methoxy, ethoxy, allyloxy, isopropoxy, butoxy, isobutoxy, methoxyethyl, alkoxy, phenoxy, azido, amino, alkylamino, fluoro, chloro and bromo. Nucleosides and nucleotides include the natural D configurational isomer (D-form), as well as the L configurational isomer (L-form) (Beigelman, U.S. Pat. No. 6,251,666; Chu, U.S. Pat. No. 5,753,789; Shudo, EP0540742; Garbesi et al., Nucl. Acids Res., 21:4159-4165 (1993); Fujimori, J. Amer. Chem. Soc., 112:7435 (1990); Urata, (1993) Nucleic Acids Symposium Ser. No. 29:69-70).

The term "nucleotide" as used herein means a nucleoside in a phosphorylated form—a phosphate ester of a nucleoside, as a monomer unit or within a polynucleotide polymer. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group may include sulfur substitutions for the various oxygen moieties, e.g., α-thio-nucleotide 5'-triphosphates. Nucleotides can exist in the mono-, di-, or tri-phosphorylated forms. The carbon atoms of the ribose present in nucleotides are designated with a prime character (') to distinguish them from the backbone numbering in the bases. For a review of polynucleotide and nucleic acid chemistry, see Shabarova, Z. and Bogdanov, A. Advanced Organic Chemistry of Nucleic Acids, VCH, New York, 1994.

The terms "polynucleotide" and "oligonucleotide" are used interchangeably and mean a single-stranded or double-stranded polymer of nucleotide monomers, including 2'-deoxyribonucleotides (DNA) and ribonucleotides (RNA), linked by internucleotide phosphodiester bond linkages, including linear structures, branched structures, or internucleotide analogs. A "polynucleotide sequence" refers to the sequence or order of particular nucleotide monomers along the polymer. "Polynucleotides" are not limited to any particular length of nucleotide sequence, as the term "polynucleotides" encompasses polymeric forms of nucleotides of any length. Polynucleotides that range in size from about 5 to about 40 monomeric units are typically referred to in the art as oligonucleotides. Polynucleotides that are several thousands or more monomeric nucleotide units in length are typically referred to as nucleic acids. Polynucleotides can be linear, branched linear, or circular molecules. Polynucleotides also have associated counter ions, such as H$^+$, NH$_4^+$, trialkylammonium, Mg$^{2+}$, Na$^+$ and the like.

Polynucleotides that are formed by 5'-3' phosphodiester linkages are said to have 5'-ends and 3'-ends because the mononucleotides that are reacted to make the polynucleotide are joined in such a manner that the 5' phosphate of one mononucleotide pentose ring is attached to the 3' oxygen (i.e., hydroxyl) of its neighbor in one direction via the phosphodiester linkage. Thus, the 5'-end of a polynucleotide molecule has a free phosphate group or a hydroxyl at the 5' position of the pentose ring of the nucleotide, while the 3' end of the polynucleotide molecule has a free phosphate or hydroxyl group at the 3' position of the pentose ring. Within a polynucleotide molecule, a position or sequence that is oriented 5' relative to another position or sequence is said to be located "upstream," while a position that is 3' to another position is said to be "downstream." This terminology reflects the fact that polymerases proceed and extend a polynucleotide chain in a 5' to 3' fashion along the template strand.

A polynucleotide may be composed entirely of deoxyribonucleotides, entirely of ribonucleotides, or chimeric mixtures thereof. Polynucleotides may be composed of internucleotide nucleobase and sugar analogs. Unless denoted otherwise, whenever a polynucleotide sequence is represented, it will be understood that the nucleotides are in 5' to 3' orientation from left to right.

The term "oligonucleotide" refers to a shorter polynucleotide having a length of less than about 100 nucleotides, but more typically having from 10 to 35 nucleotides, which is capable of hybridizing to a genomic DNA molecule, a cDNA molecule, or an mRNA, or other nucleic acid of interest. Oligonucleotides can be labeled, e.g., with $^{32}$P-nucleotides or nucleotides to which a label, such as biotin or a fluorescent dye (for example, Cy3 or Cy5) has been covalently conjugated. In one embodiment, a labeled oligonucleotide can be used as a probe to detect the presence of a nucleic acid. In another embodiment, oligonucleotides (one or both of which may be labeled) can be used as a primer to initiate synthesis of a second polynucleotide strand using the polynucleotide to which the primer hybridizes as a template.

Generally, oligonucleotides are prepared synthetically, preferably on a nucleic acid synthesizer. Accordingly, oligonucleotides can be prepared with non-naturally occurring phosphoester analog bonds, such as thioester bonds, etc.

Specific examples of synthetic oligonucleotides include oligonucleotides that contain phosphorothioates, phosphotriesters, methyl phosphonates, short chain alkyl, or cycloalkyl intersugar linkages or short chain heteroatomic or heterocyclic intersugar linkages. Most preferred are those with $CH_2$—NH—O—$CH_2$, $CH_2$—$N(CH_3)$—O—$CH_2$, $CH_2$—O—N$(CH_3)$—$CH_2$, $CH_2$—$N(CH_3)$—$N(CH_3)$—$CH_2$ and O—N$(CH_3)$—$CH_2$—$CH_2$ backbones (where phosphodiester is O—$PO_2$—O—$CH_2$). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science 254:1497 (1991)). Other synthetic oligonucleotides may contain substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; CF3; OCF3; O-; S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine may be used, such as inosine.

Oligonucleotide molecules (either a primer or probe) is capable of hybridizing to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50 9.51). For hybridization with shorter nucleic acids, i.e., oligonucleotides, the position of mismatches becomes more important, and the length of the oligonucleotide determines its specificity (see Sambrook et al., supra, 11.7 11.8).

The term "primer" and "extension primer" mean an oligonucleotide, whether occurring naturally, as in a purified restriction digest, or produced synthetically, that is complementary to a target sequence and is capable of functioning as the point of initiation of DNA synthesis upon annealing to a complementary under appropriate conditions, which include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The term "primer" may include one or more primer.

Primers are preferably single stranded for maximum efficiency in amplification, but may alternatively be double stranded. If double stranded, the primer is first treated to separate its strands before being used to prepare extension products. Preferably, the primer is an oligodeoxyribonucleotide (also referred to as an "oligonucleotide" or "oligo"). The primer must be sufficiently long to prime the synthesis of extension products in the presence of the agent for polymerization. The exact lengths of the primers will depend on many factors, including temperature and source of primer and use of the method. For example, depending on the complexity of the target sequence, the oligonucleotide primer typically contains from 15-35 nucleotides, although it may contain more or fewer nucleotides. Short primer molecules generally require lower temperatures to form sufficiently stable hybrid complexes with the template. A primer need not complement the exact sequence of the template but must be sufficiently complementary to hybridize with a template. Primers can incorporate additional features which allow for the detection or immobilization of the primer but do not alter the basic property of the primer, that of acting as a point of initiation of DNA synthesis. For example, primers may consist of one or more oligonucleotides which contain mismatches with some or all members of a given set of target sequence variants, but contain sufficient regions of complementarity to each target sequence variant so as to enable hybridization with all target sequence variants under suitable conditions.

Primers, once hybridized to a nucleic acid sequence (DNA, RNA or DNA-RNA chimeric molecule) that is substantially complementary, may function in amplification methods of the invention as substrates for a polymerase. The 3'-OH end of these substrates can be elongated, in the presence of adequate nucleotides and a polymerase, leading to synthesis of a strand complementary to the template sequence on which said primer is hybridized. A primer can also be constituted by hybridizing the end of a single-stranded nucleic acid sequence on itself, leading in particular to formation of hairpin or stem-loop structures. Computer programs are useful in the design of primers with the required specificity and optimal amplification properties. See, e.g., Oligo version 6.0 (Molecular Biology Insights, Inc.).

Primers are used in any one of a number of template dependent processes to amplify the target-gene sequences present in a given template sample. The most widely used amplification method is PCR, which is described in detail in U.S. Pat. Nos. 4,683,195, 4,683,202 and 4,800,159, each of which is incorporated herein by reference.

The term "probe," as used herein, means a polynucleotide fragment that is capable of hybridizing to a complementary nucleic acid template to form a double stranded complex due to complementarity of nucleotide sequence in the probe with a nucleotide sequence in the template. A probe typically contains a detectable radioactive or chemical label enabling detection of the probe by any of various means known to those in the art. As used herein, the term "probe" specifically refers to a polynucleotide fragment that is blocked at the 3' end, for example, with a 2'-,3'-dideoxynucleotide (i.e., there is no free 3' hydroxyl group) or with a phosphate group.

The abbreviation "Tm" means the "melting temperature" or "annealing temperature" of a nucleic acid duplex. The melting temperature is the temperature at which half of a population of double-stranded polynucleotide molecules or nucleobase oligomers, in homoduplexes or heteroduplexes, become dissociated into single strands. The Tm of a double-stranded nucleobase oligomeric molecule is influenced by the types of bases, the base sequence, structure of the oligomeric linkages, and the presence of non-natural features in the sequence, such as artificial linkages. Methods for calculating or experimentally determining Tm are well-known known in the art. See, for example, Breslauer et al., *Proc. Natl. Acad. Sci. USA* 83: 3746-3750 (1986); Baldino et al., *Methods in Enzymol.* 168: 761-777 (1989); and Breslauer, *Methods in Enzymol.* 259: 221-242 (1995). Those skilled in the art of nucleic acid technology can determine duplex stability empirically considering a number of variables including, for example, the length of the oligonucleotide, base composition and sequence of the oligonucleotide, ionic strength, and incidence of mismatched base pairs.

The practice of the present invention will employ, unless otherwise indicated, conventional techniques of molecular biology, microbiology, recombinant DNA techniques, and oligonucleotide synthesis which are within the skill of the art. Such techniques are explained fully in the literature. Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See, e.g., Sambrook et al., Molecular Cloning: A Laboratory Manual (2d ed., Cold Spring Harbor Laboratory Press, Cold Spring Harbor, N.Y. (1989)); Oligonucleotide Synthesis (M. J. Gait, ed., 1984); Nucleic Acid Hybridization (B. D. Hames & S. J. Higgins, eds., 1984); A Practical Guide to Molecular Cloning (B. Perbal, 1984); and a series, Methods in Enzymology (Academic Press, Inc.), the contents of which are incorporated herein by reference.

The present invention is directed to methods for allele-specific PCR (AS-PCR) amplification of a polynucleotide sequence to selectively or preferentially amplify a specific polynucleotide segment relative to another polynucleotide segment on the basis of one or more nucleotide differences. More particularly, the present invention relates to methods for improving the ability of allele-specific PCR to discriminate between two alleles that differ by one or more nucleotides, using allele-specific PCR amplification. The methods of the invention are particularly useful, for example, for selectively amplifying a polynucleotide sequence having one of two or more known alleles in order to determine which allele is present. The discriminatory capability of the methods of the invention enable selective amplification of polynucleotide sequences having differences of only a single nucleotide polymorphism.

The use of allele-specific PCR to detect the presence or absence of a particular known allele is made possible by the use of the oligonucleotides of the present invention, which incorporate a locked nucleic acid (LNA) unit and a mismatch nucleobase and an allele-specific nucleobase. The oligonucleotides and methods described herein effectively suppress extension of the incorrect allele, while favoring the correct specific allele.

The present invention is generally directed to oligonucleotides that are complementary to a target polynucleotide and comprise a locked nucleic acid (LNA) unit, a mismatch nucleobase, and an allele-specific nucleobase. Preferably, the allele-specific nucleobase corresponds to one allele of the target polynucleotide. However, it is understood that the allele-specific nucleobase may constitute a mismatch relative to all alleles of the target polynucleotide at that particular locus.

In another aspect, the present invention includes duplexes comprising an oligonucleotide hybridized to a target polynucleotide, wherein the oligonucleotide is complementary to the target polynucleotide and comprises an LNA unit, a mismatch nucleobase and an allele-specific nucleobase corresponding to an allele of the target polynucleotide.

In another aspect, the present invention includes a method of detecting the presence or absence of a target polynucleotide in a biological sample, comprising:

(a) providing an oligonucleotide complementary to a target polynucleotide, wherein the oligonucleotide comprises an LNA unit, a mismatch nucleobase, and an allele-specific nucleobase corresponding to an allele of the target polynucleotide;

(b) combining the oligonucleotide of (a) with a biological sample suspected of containing the target polynucleotide;

(c) detecting the presence or absence of hybridization and extension of the oligonucleotide with the target polynucleotide, wherein hybridization and extension of the oligonucleotide with the target polynucleotide is indicative of the presence of an allele corresponding to the allele-specific nucleobase.

In another aspect, the present invention includes a method of detecting the presence or absence of a polymorphism in a target nucleotide in a biological sample, comprising:

(a) providing an oligonucleotide primer complementary to a target polynucleotide, wherein the oligonucleotide primer comprises an LNA unit, a mismatch nucleobase, and an allele-specific nucleobase corresponding to an allele of the target polynucleotide;

(b) combining the oligonucleotide primer of (a) and a polymerase enzyme with a biological sample suspected of containing a target polynucleotide under conditions amenable to hybridization of the oligonucleotide primer with the target polynucleotide and synthesis of a primer extension product;

(c) detecting the presence or absence of a primer extension product, wherein the presence of a primer extension product is indicative of the presence of an allele corresponding to the allele-specific nucleobase.

In yet another aspect, the present invention includes a method of quantitatively determining the frequency of a first allele and a second allele of a target polynucleotide in a biological sample, comprising:

(a) amplifying a target polynucleotide in a biological sample using a first oligonucleotide complementary to a first allele of the target polynucleotide, wherein the first oligonucleotide comprises an LNA unit, a mismatch nucleobase, and an allele-specific nucleobase corresponding to a first allele of the target polynucleotide;

(b) amplifying a target polynucleotide in a biological sample using a second oligonucleotide complementary to a second allele of the target polynucleotide, wherein the second oligonucleotide comprises an LNA unit, a mismatch nucleobase, and an allele-specific nucleobase corresponding to a second allele of the target polynucleotide;

(c) comparing the cycle threshold for the amplification of (a) and (b);

(d) determining the frequency of the first allele and the second allele.

In another aspect, the present invention includes a method of quantitatively determining the frequency of an allele of a target polynucleotide in a biological sample, comprising:

(a) amplifying a target polynucleotide in a biological sample using a first oligonucleotide complementary to an allele of the target polynucleotide, wherein the first oligonucleotide comprises an LNA unit, a mismatch nucleobase, and an allele-specific nucleobase corresponding to a first allele of the target polynucleotide;

(b) calculating the cycle threshold for (a);

(c) comparing the cycle threshold for (a) with the cycle threshold for amplification of a known standard;

(d) determining the frequency of the allele.

In some embodiments of the invention, the LNA unit and the mismatch nucleobase are contiguous. In other embodiments, the mismatch nucleobase and the allele-specific nucleobase are contiguous. In other embodiments, the LNA unit, the mismatch nucleobase and the allele-specific nucleobase are contiguous.

In a particular embodiment of the invention, the LNA unit is at the −2 position relative to the allele-specific nucleobase. In another particular embodiment of the invention, the mismatch nucleobase is at the −1 position relative to the allele-specific nucleobase. In yet another particular embodiment, the LNA unit is at the −2 position and the mismatch nucleobase is at the −1 position relative to the allele-specific nucleobase.

In still another embodiment, the allele-specific nucleobase is at the 3' terminal position. In still another embodiment, the allele-specific nucleobase is at the 3' terminal position and the LNA unit is at the −2 position relative to the allele-specific nucleobase. In another particular embodiment, the allele-specific nucleobase is at the 3' terminal position and the mismatch nucleobase is at the −1 position relative to the allele-specific nucleobase.

In a more particular embodiment, the allele-specific nucleobase is at the 3' terminal position, the LNA unit is at the −2 position and the mismatch nucleobase is at the −1 position relative to the allele-specific nucleobase.

In some embodiments of the invention, the allele-specific nucleobase is complementary to the target polynucleotide. In other embodiments, the allele-specific nucleobase is non-complementary to the target polynucleotide.

In other embodiments of the invention, the oligonucleotide is a primer.

PCR Amplification

The present invention is directed to a process for selectively amplifying and discriminating any one or more specific nucleic acid sequences from polymorphic variants of such sequences, using the technique of polymerase chain reaction (or PCR). Polymerase chain reaction (PCR) is very widely known in the art. For example, U.S. Pat. Nos. 4,683,195, 4,683,202, and 4,800,159; K. Mullis, Cold Spring Harbor Symp. Quant. Biol., 51:263-273 (1986); and C. R. Newton & A. Graham, Introduction to Biotechniques: PCR, 2.sup.nd Ed., Springer-Verlag (New York: 1997), the disclosures of which are incorporated herein by reference, describe processes to amplify a nucleic acid sample target using PCR amplification extension primers which hybridize with the sample target. As the PCR amplification primers are extended, using a DNA polymerase (preferably thermostable), more sample target is made so that more primers can be used to repeat the process, thus amplifying the sample target sequence. Typically, the reaction conditions are cycled between those conducive to hybridization and nucleic acid polymerization, and those that result in the denaturation of duplex molecules.

To briefly summarize, in the first step of the reaction, the nucleic acid molecules of the sample are transiently heated, and then cooled, in order to denature double stranded molecules. Forward and reverse primers are present in the amplification reaction mixture at an excess concentration relative to the sample target. When the sample is incubated under conditions conducive to hybridization and polymerization, the primers hybridize to the complementary strand of the nucleic acid molecule at a position 3' to the sequence of the region desired to be amplified that is the complement of the sequence whose amplification is desired. Upon hybridization, the 3' ends of the primers are extended by the polymerase. The extension of the primer results in the synthesis of a DNA molecule having the exact sequence of the complement of the desired nucleic acid sample target. The PCR reaction is capable of exponentially amplifying the desired nucleic acid sequences, with a near doubling of the number of molecules having the desired sequence in each cycle. Thus, by permitting cycles of hybridization, polymerization, and denaturation, an exponential increase in the concentration of the desired nucleic acid molecule can be achieved.

Preparation of Polynucleotide Templates

Any specific nucleic acid sequence can be amplified by the present process. It is only necessary that a sufficient number of bases at both ends of the sequence be known so that two primers can be prepared which will hybridize to different strands of the desired sequence and at relative positions along the sequence such that an extension product synthesized from one primer, when it is separated from its template (complement), can serve as a template for extension of the other primer into a nucleic acid of defined length. The greater the knowledge of the bases at both ends of the sequence, the greater can be the specificity of the primers for the target nucleic acid sequence, and thus the greater the efficiency of the process.

Any polynucleotide molecule, in purified or nonpurified form, can be utilized as the starting nucleic acid or acids, provided it contains the sequence being detected. Thus, the process may employ, for example, DNA or RNA, including messenger RNA, which DNA or RNA may be single stranded or double stranded. In addition, a DNA-RNA hybrid which contains one strand of each may be utilized. A mixture of any of these nucleic acids may also be employed, or the nucleic acids produced from a previous amplification reaction herein using the same or different primers may be so utilized. The specific nucleic acid sequence to be amplified may be only a fraction of a larger molecule or can be present initially as a discrete molecule, so that the specific sequence constitutes the entire nucleic acid.

It is not necessary that the sequence to be amplified be present initially in a pure form; it may be a minor fraction of a complex mixture, such as a portion of the beta-globin gene contained in whole human genomic DNA, or a portion of nucleic acid sequence due to a particular microorganism which organism might constitute only a very minor fraction of a particular biological sample. The starting nucleic acid may contain more than one desired specific nucleic acid sequence which may be the same or different. Therefore, the present process is useful not only for producing large amounts of one specific nucleic acid sequence, but also for amplifying simultaneously more than one different specific nucleic acid sequence located on the same or different nucleic acid molecules if more than one of the base pair variations in sequence is present.

The nucleic acid templates may be obtained from any source, for example, from plasmids such as pBR322, from cloned DNA or RNA, or from natural DNA or RNA from any source, including bacteria, yeast, viruses, organelles, and higher organisms such as plants or animals. DNA or RNA may be extracted from blood, tissue material such as chorionic villi or amniotic cells by a variety of techniques such as that described by Maniatis et al., Molecular Cloning (1982), 280-281. The method of the present invention are particularly useful in analyzing genomic DNA.

The cells may be directly used without purification of the nucleic acid if they are suspended in hypotonic buffer and heated to about 90°-100° C., until cell lysis and dispersion of intracellular components occur, generally about 1 to 15 minutes. After the heating step the amplification reagents may be added directly to the lysed cells. This direct cell detection method may be used on peripheral blood lymphocytes and amniocytes.

The target nucleic acid contained in the sample may be in the form of genomic DNA, or alternatively may be first reverse transcribed into cDNA, if necessary, and then denatured, using any suitable denaturing method, including physical, chemical, or enzymatic means, which are known to those of skill in the art. A preferred physical means for strand separation involves heating the nucleic acid until it is completely (>99%) denatured. Typical heat denaturation involves temperatures ranging from about 80° C. to about 105° C., for times ranging from a few seconds to minutes. As an alternative to denaturation, the target nucleic acid may exist in a single-stranded form in the sample, such as, for example, single-stranded RNA or DNA viruses.

The denatured nucleic acid strands are then incubated with preselected oligonucleotide primers, and, optionally, a labeled oligonucleotide (referred to herein as a "probe") for purposes of detecting the amplified sequence) under conditions that facilitate the binding of the primers and probes to the single nucleic acid strands. As known in the art, the primers are selected so that their relative positions along a duplex sequence are such that an extension product synthesized from one primer, when the extension product is separated from its template (complement), serves as a template for the extension of the other primer to yield a replicate chain of defined length.

PCR Extension Primers

In the methods of the present invention, PCR amplification is performed using extension primers that span the region encompassing the allele. Extension primers must be sufficiently long to prime the synthesis of extension products in the presence of the agent for polymerization. The exact length and composition of the primer will depend on many factors, including temperature of the annealing reaction, and the source and composition of the primer. For example, depending on the complexity of the target sequence, the oligonucleotide primer typically contains about 15-30 nucleotides, although a primer may contain more or fewer nucleotides. Preferably, primers will contain around 20-25 nucleotides. The primers must be sufficiently complementary to anneal to their respective strands selectively and form stable duplexes.

In the context of the present invention, allele-specific PCR is performed for the purpose of discriminating between two or more alleles of a genetic locus that differ by a single or multiple nucleotide polymorphism. A forward extension primer used will be complementary to one allele, but differ from the other alleles. Specifically, the forward extension primer will have a sequence complementary to a region encompassing the target allele, with the last 3' nucleotide of the forward extension primer being exactly complementary to one of the known alleles of the target sequence, but differing from the variant allele by one or more nucleotide at the 3' terminus of the primer. As a result of the nucleotide mismatch between the 3' terminus of the primer and the 5' initiation point of the template, the exactly matching primer will preferentially hybridize and extend under appropriate PCR conditions over the mismatching primer.

The method of the present invention also contemplates PCR amplification using a reverse extension primer having a sequence complementary to a separate region common to both genes of the target allele and the variant allele, but which is located at a locus remote from the specific genetic locus of the target allele and variant allele. The reverse extension primer will have the opposite orientation relative to the forward extension primer. The forward and reverse extension primers thus define a region of DNA that will be amplified when subjected to PCR amplification conditions. The reverse extension primer is preferably complementary to a polynucleotide sequence that is common to both the gene of the target allele and the gene of the variant allele at a position located downstream (in the 3' direction) from the multi-allelic genetic locus of interest.

The allele-specific primers used in the method of the present invention need not reflect the exact sequence of the template, but must be sufficiently complementary to hybridize selectively to their respective strands. Non-complementary bases or longer sequences can be interspersed into the primer or located at the 5' end of the primer, provided the primer retains sufficient complementarity with a template strand to form a stable duplex.

Allele-Specific PCR Amplification

The present invention contemplates use of the PCR-based method for determining the presence or absence of a specific known nucleic acid sequence, such as a mutation (e.g. a genetic polymorphism), called allele-specific PCR (AS-PCR or ASP) or allele-specific amplification (ASA), also known as amplification refractory mutation system (ARMS) and PCR amplification of specific alleles (PASA), as described in U.S. Pat. No. 5,639,611; Ruano et al., Nucleic Acids Res 17:8392 (1989) (allele-specific amplification), Ruano et al., Nucleic Acids Res. 19:5887-5882 (1991) (coupled amplification and sequencing) and Cheng et al., Nature 368:664-665 (1994). Allele-specific PCR amplification (ASA) is used to selectively amplify one specific predetermined allele from a sample containing multiple alleles at the same genetic locus.

In a typical ASP assay one or more PCR reactions using different PCR extension primers are annealed to the same nucleic acid sample. The PCR primers are designed to have a residue at the 3'-terminus of the primer (complementary to the 5' primer initiation site of the template) that is complementary to one of the two allelic variants and not to the other. The PCR reaction does not extend from a primer having a 3'-terminal mismatched base, unless the polymerase used has a proof-reading activity that removes the mismatched base and inserts the correct base. Proofreading repairs the PCR primer and destroys the extension discrimination between the two alleles. Therefore, a polymerase lacking 3'→5' proofreading activity, such as Taq DNA polymerase has traditionally been used in an AS-PCR assay.

Although discrimination between specificity of PCR extension from the allele-specific AS-PCR primers is known to be enhanced by the introduction of deliberate multiple mismatches near the 3'-terminal nucleotide, this significantly reduces the overall PCR extension product yield. See, e.g., Ruano et al., Nucleic Acids Res. 17:8392 (1989). Other factors known to affect the stability of the hybridization of PCR primers in an ARMS assay include the position of additional mismatches in the primer, the GC content of the 5 or 6 nucleotides preceding the 3' nucleotide, and the discriminatory 3'-terminal nucleotide, depending on the difference between the alleles and the type of mismatch. The destabilization is greater when the second mismatch is nearer to the 3'-terminal nucleotide. The destabilizing effect of additional mismatches on ASP has been ranked qualitatively (CC>CT>GG=AA=AC>GT). In contrast, the method of the present invention has been shown to be effective in discriminating on the basis of a single nucleotide mismatch when performed under appropriate PCR amplification conditions, as described below.

In the present invention, a polynucleotide segment is selectively amplified using the oligonucleotides of the present invention. The primers are combined with a dNTP mixture and appropriate polymerase enzyme having exonuclease activity, and the polynucleotide segment is amplified under polymerase chain reaction conditions, wherein stability of the 3' end of the allele-specific extension primer is conferred by the presence of the LNA with specificity determined by the additional mismatched nucleotide. These conditions result in selective hybridization of the allele-specific extension primer to the target allele and extension of said primer, relative to the variant allele.

PCR Conditions

The allele-specific amplification method of the present invention is performed under standard conditions used for PCR. The predicted Tm is calculated using standard algorithms, such as the nearest neighbor algorithm (Von-Ahsen et al., Clinical Chemistry 45(12):2094-2101 (1999).

Detection of PCR Amplification Products

Allele-specific amplification can be detected during extension of the allele-specific primer using any suitable kinetic PCR platform, or post-PCR by agarose gel electrophoresis, for example. Examples of suitable detection systems and platforms include, but are not limited to: single nucleotide extension (Orchid), melting of fluorescent probes (Roche, Epoch), hybridization blots (Innova, Roche), oligonucleotide microarray on various support (Nanogen, Luminex, Motorola), Taqman probes (Applied Biosystems), lux primers (Invitrogen). Many other methods are known to those in the art that can be used for detecting PCR amplification products produced during or after amplification in accordance with the present invention.

In detecting PCR amplification products, each allele is analyzed independently, avoiding problems associated with allele-specific primers competing with each other. For example, first the "disease related" allele is specifically amplified followed by amplification of the wild-type allele. The ratio of product produced by each allele-specific primer during the linear phase of PCR amplification is proportional to the amount of starting material, and thus the frequency of each target allele.

Applications of Allele-Specific PCR

The allele-specific PCR method of the present invention may be used to selectively amplify a polynucleotide sequence of any gene derived from any prokaryotic or eukaryotic organism, including, but not limited to, plants or animals, in particular humans. The method of the present invention is particularly useful for haplotyping genes derived from a diploid organisms (which have two copies of each gene, one copy inherited from each parent). Allele-specific PCR is particularly useful in the field of human genetics (to identify the genetic determinants of complex diseases), anthropology (to identify haplotypes associated with particular populations and thereby determination of the origin and migration patterns of human populations).

The present invention is also useful in the field of molecular diagnostics for determination of genotypes of mutations or polymorphisms associated with diseases, minimal residual disease after chemotherapy, pharmacogenomics & pharmacogenetics, cancer genetics, and infectious diseases. The present invention is also useful in the field of pharmacogenetics, for use in correlating specific individual genetic polymorphisms and individual responses to specific pharmaceutical compound. The present invention is also useful for haplotyping of oncogenes or tumor suppressor genes, which may be associated with cancer susceptibility. Currently, haplotypes in populations are determined using statistical methods.

Uses of the Invention

The present invention relates to novel primers for allele specific PCR which incorporate a locked nucleic acid (LNA) at the –2 position of the primer and a base mismatch at the –1 position of the primer. The 3' base is the SNP that is being tested for. In cases where the SNP is present, the primer will anneal and PCR can be used to specifically amplify SNP containing sequences. This primer design appears to have advantages for sensitive quantitation of SNPs, for instance in quantitating the emergence of mutation associated drug resistance in leukemia, or other situations where the sequence of interest is present at a very low level. LNA and engineered mismatches have both been used in primer design for AS-PCR, but the synergistic effect of using primers which contain both modifications has not been previously described. Several combinations of base mismatches and LNA position were tried before arriving at successful combinations, including the optimized –2 LNA, –1 mismatch combination. However, LNA/base mismatch combinations other than the ones described here also result in improved discrimination. Allele-specific primer extension may also be optimized for particular sequences by comparing different combinations of LNA/base mismatch to be tested.

A unique primer for allele specific PCR (AS-PCR) is designed using a –2 locked nucleic acid (LNA) and a –1 mutation (identical to complement strand) with broad application for any quantitative Real Time PCR. This primer is shown to be useful for specific detection of SNP changes using any Real Time platform, i.e., ABI, Light Cycler, etc.

Generally, AS-PCR has been used solely for qualitative detection of alleles but not quantitation. The present invention provides a simple method for allele-specific primer design which significantly improves allele discrimination and does not require extensive optimization of PCR amplification conditions. Further, the methods of the invention are simple, low cost, and can be readily performed in any lab using any Real Time platform.

Quantitation of any SNP is useful for many purposes, for example, determining the proportion of cells carrying a somatic mutation or genetic mosaicism, the proportion of fetal cells in maternal circulation, detection of minimal residual disease as seen by somatic mutation such as reduction of malignant cells by chemotherapy or reappearance of resistant clone, and rapid monitoring of efficacy of new drugs using both "in vitro" systems as well as clinical trials. The application of this assay can be used, for example, for detection of minimal residual disease caused by somatic mutations such as those causing malignancies, monitoring of heteroplasty and homoplasty of disorders caused by mitochondrial mutations causing diseases, monitoring RH fetal incompatibility and its treatment, monitoring of progression and efficacy of therapy of infectious diseases, monitoring of resistant clones such as in HIV infection and its treatment, monitoring of leukemias and other disorders caused by somatic mutations, monitoring of efficacy of transplantation interventions, etc.

The oligonucleotides of the present invention may be used to quantitatively measure a SNP allele frequency in a mixture of DNAs pooled from individual samples by measuring the relative amounts of the two allelic variants of a SNP in pooled samples of DNA. This can be an accurate estimate of the frequency of the alleles in the population from which the samples were drawn. In this approach, equal aliquots of the pool are divided between two PCR reactions, each of which contains a primer pair specific to one or the other SNP allelic variant. The specificity of the PCR amplification is conferred by using the oligonucleotides of the present invention, which include a 3' allele-specific nucleobase that corresponds to one or the other of the variant nucleotides, and have enhanced specificity and ability to discriminate between alleles. Ideally, only completely matched primers are extended, and only the matching allele is amplified. In practice, however, there will be amplification of the mismatched allele, but this will occur much less efficiently such that many more amplification cycles are needed to generate detectable levels of product. Mismatch amplification is frequently delayed by >10 cycles when amplification is monitored on a cycle-by-cycle basis, using fluorescent dsDNA binding dyes such as SYBR Green I. A delay of around six cycles is adequate for the determination of allele frequencies of SNPs for which the frequency of the minor allele is greater than a few percent.

When the allele frequency is 50%, one expects that each of the two PCR amplifications will require the same number of cycles to produce the same fluorescent signal, assuming that both allele-specific primers amplify with equal efficiency. The number of cycles before a reaction crosses a predetermined threshold, the $C_t$, can be fractional. When one allele is more frequent, amplification of that allele will reach the threshold at an earlier cycle, that is, have a smaller $C_t$. The difference in $C_t$'s between the two PCR reactions, the $\Delta C_t$, is a measure of the bias and thus of the allele frequency. A one-cycle delay means that the ratio of the amount of one allele to the other is 1:2; a two-cycle delay, 1:4; or in general, 1:$2^{\Delta C_t}$. Converting a ratio to a frequency by adding the numerator to the denominator results, as described in the Examples below.

$\Delta C_t$ can be either positive or negative, depending on which specific PCR exhibits the lowest $C_t$. The "2" in the denominator is properly "1+the initial replication efficiency". However, the initial replication efficiency is usually close to 100% so that "2" is an adequate approximation. The amplification efficiencies for the two allele-specific PCRs may differ slightly. This can be measured and compensated for by performing the assay on a DNA known to be heterozygous for the SNP of interest. The AC, for this DNA should equal zero if the PCRs are equally efficient. Any deviation from zero indicates that they are not. This deviation can then be subtracted from all AC, measurements to compensate for differential amplification efficiencies.

Kits

In another aspect, kits are provided that comprise the oligonucleotides of the present invention. As disclosed in detail above, the oligonucleotides that may be used in such kits are complementary to a target polynucleotide, wherein the oligonucleotide comprises an LNA unit, a mismatch nucleobase, and an allele-specific nucleobase corresponding to an allele of the target polynucleotide. The oligonucleotides utilized in kits may include any of the oligonucleotides disclosed above.

The kits of the invention may also include reagents necessary or useful for the amplification of target polynucleotides, which may include one or more of the following: polymerase enzymes, primer extension deoxynucleotide triphosphates, and primer termination dideoxynucleotide triphosphates, and any buffers or other solutions generally used in PCR amplification reactions and kits.

The following examples illustrate how the invention may be practically applied. It is understood, of course, that the following examples are provided for the sole purpose illustrating particular applications, and that other applications are contemplated and will be appreciated by those skilled in the art. These examples are not, therefore, to be construed as limiting the scope of the invention.

Example 1

To illustrate the utility of the present invention, the G1898T SNP somatic mutation of JAK2 was quantitated and the sensitivity, specificity and reproducibility of detection using more than one Real Time platform was demonstrated. Any derivation from the complementary primer at −1 position from the polymorphic site, together with a −2 LNA, provides optimal performance. Thus, the −2 LNA assists in stabilizing the 3' end, while −1 provides specificity but not stability.

Myeloproliferative disorders (MPDs) are hematological malignancies due to clonal proliferation arising from a single multilineage stem cell. The World Health Organization (WHO) classified MPDs into the following four prototypical clinical diseases: polycythemia vera (PV), essential thrombocythemia (ET), myelofibrosis with myeloid metaplasia (MMM), and chronic myeloid leukemia (CML). Subsequently, other related disorders were added to this classification (1). The chromosomal translocation t(9,22) resulting in a chimeric fusion protein encoded by the Bcr-Abl gene, leads to proliferation and survival of myeloid progenitor cells in CML. Recently, a novel somatic single point mutation in the 9p chromosomal region encoding the tyrosine kinase JAK2 (1849 G to T) has been reported in several MPDs (2-6). This mutation results in a non-synonymous amino acid substitution at position 617 (valine to phenylalanine) located in the JH2 pseudo-kinase auto-inhibitory domain (7). The mutation renders the enzyme constitutively active and leads to cytokine hypersensitivity and erythrocytosis in a mouse model (8). The JAK2$^{V617F}$ mutation has been reported in greater than 80% of PV patients and in approximately half of ET or MMM patients (5). The proportion of the mutant allele is highly variable, with approximately 30% of PV patients having loss-of-heterozygosity of chromosome 9p created in most instances by uniparenteral disomy (9).

Studies in MPD support that acquisition of the JAK2$^{V617F}$ mutation results from a somatic event. The proportion of JAK2 mutant allele in a clonal granulocyte cell population from the peripheral blood of a patient, can vary from 0 to 100%. According to one scenario, the mutation is not the first event leading to disease. This is further supported by the existence of PV families with a predisposition to acquire PV (10). In addition, zygosity in patients carrying the JAK2$^{V617F}$ mutation can be heterogeneous, with wild-type, heterozygous, and mutant homozygous clones being present. The clinical significance and role of the JAK2 mutation in the pathology and progression of disease, especially for PV, is being investigated. It appears that some complications of MPDs such as the degree of marrow fibrosis or thrombotic tendencies correlate with overall proportion of the mutant allele in circulating cells (8, 11). The close association of JAK2$^{V617F}$ with PV and BFU-E endogenous colonies of PV makes this mutation an excellent disease marker. Hence, disease progression, treatment, and development of novel chemotherapeutics can be readily assessed by following changes in the proportion of the mutant JAK2 allele in clonal granulocytes.

To date, several different methods have been developed to quantitatively determine the proportion of single nucleotide polymorphisms (SNPs) in pooled DNA samples (12). These include (but are not limited to) allele-specific PCR (AS-PCR) and pyrosequencing. A number of strategies have been employed to improve the specificity and reliability of AS-PCR and adapt it to real-time monitoring. These modifications have demonstrated that AS-PCR can be a reliable tool for genotyping provided time is taken to carefully design and optimize PCR conditions. On the other hand, pyrosequencing requires instrumentation that is not readily available and setup costs are prohibitive for routine laboratory testing. Moreover, pyrosequencing cannot be used for routine screening of residual or early disease, since the proportion of the JAK2 mutant allele is below the 5% detection limit threshold.

The following describes the development of a novel approach to quantitatively determine the proportion of wild-type (wt) and mutant JAK2 alleles by a novel modification of real-time AS-PCR. The methods described herein provide high sensitivity, specificity, and reproducibility which permits accurate quantitation of the JAK2$^{V617F}$ mutant allele using now widely available kinetic PCR instrumentation. Moreover, this approach to allele-specific primer design is simple, does not require optimization of PCR conditions, and incorporates nucleotides that are readily available from most oligonucleotide synthesis companies. This methodology was used to provide definitive evidence that the JAK2$^{V617F}$ mutation is not the PV initiating event.

Materials and Methods

Samples. Blood samples were collected from 20 unrelated PV patients and 3 healthy volunteers using an IRB approved protocol. Granulocytes were isolated from peripheral blood using standard methods. Genomic DNA (gDNA) was extracted from peripheral blood leukocytes and purified granulocytes using the Puregene DNA purification kit as recommended by the manufacturer (Gentra, Minneapolis, Minn.).

BFU-E colony culture. In vitro assay of erythroid progenitors' responsiveness to erythropoietin (Epo) was performed as previously described (13). Briefly, mononuclear cells from peripheral blood were isolated on Histopaque 1077 (Sigma, Saint Louis, Mo.) and cultured at a final density of 3×10$^5$ cells/mL in Methocult H-4531 medium (StemCell Technologies Inc., Vancouver, Canada) in 35-mm Petri dishes in the presence or absence of 3 U/mL Epo. Cultures were maintained at 37° C. and 5% carbon dioxide. Single erythroid colonies, selected using standard criteria, were picked after 14 days in culture using micropipettes.

Real-time AS-PCR. Real-time AS-PCR was performed on an Applied Biosystems 7000 Sequence Detection System (Applied Biosystems, Foster City, Calif.). Typical reactions (25 µL) consisted of 1× TaqMan Universal PCR master mix (Applied Biosystems, Foster City, Calif.); 300 nM JAK2 universal forward and allele-specific reverse primers; 125 nM FAM labeled JAK2 MGBNFQ probe (Applied Biosystems, Foster City, Calif.); and 1-50 ng purified genomic DNA. Enzyme activation (95° C. for 10 min) was followed by 50 cycles of 95° C. for 15 sec, and 60° C. for 1 min. Allele-specific primers were designed using the software program Oligo 6.7 (Molecular Biology Insights, Inc., Cascade, Colo.) and synthesized by IDT (Integrated DNA Technologies, Coralville, Iowa). The 3' terminal sequence of the reverse primer (C or A)-gJAK2-R was selected for specific amplification of the mutant allele. Allelic discrimination was enhanced by introducing an artificial mismatch (T:T) in the −1 position starting from the 3' end of the primer, as described in the amplification refractory mutation system (ARMS, (14)). An additional modified locked nucleic acid (LNA) base (15) was placed at the −2 position (G). Control primers with either modification alone or in the absence of any modification were tested as described above. Sequences and specifications of all primers and the detection probe are provided in the following Table 1.

TABLE 1

Primer and Probe sequences.

| (A) Primer/Probe | Modification | (B) Sequence 5' to 3' |
|---|---|---|
| FAM-AS-JAK2-MGB | FAM labeled MGB probe with non-fluorescent quencher (NFQ) | 5' 6FAM - CTTGCTCATCATACTTGC - MGBNFQ 3' (SEQ ID NO: 1) |
| gJAK2-F | N/A | TTATGGACAACAGTCAAACAA CAAT (SEQ ID NO: 2) |
| G-gJAK2-R | None | TTTACTTACTCTCGTCTCCACA GAC (SEQ ID NO: 3) |

TABLE 1-continued

Primer and Probe sequences.

| (A) Primer/Probe | Modification | (B) Sequence 5' to 3' |
| --- | --- | --- |
| T-gJAK2-R | None | TTTACTTACTCTCGTCTCCACA GAA (SEQ ID NO: 4) |
| G-gJAK2-LNA-(no-1 mut)-R | LNA at -2 | TTTACTTACTCTCGTCTCCACA *G* AC (SEQ ID NO: 5) |
| T-gJAK2-LNA-(no-1 mut)-R | LNA a -2 | TTTACTTACTCTCGTCTCCACA *G* AA (SEQ ID NO: 6) |
| G-gJAK2-(-1 mut)-R | -1 Mismatch | TTTACTTACTCTCGTCTCCACA G t C (SEQ ID NO: 7) |
| T-gJAK2-(-1 mut)-R | -1 Mismatch | TTTACTTACTCTCGTCTCCACA G t A (SEQ ID NO: 8) |
| G-gJAK2-(0)LNA-R | LNA at 0 and -1 Mismatch | TTTACTTACTCTCGTCTCCACA G t *C* (SEQ ID NO: 9) |
| T-gJAK2-(0)LNA-R | LNA at 0 and -1 Mismatch | TTTACTTACTCTCGTCTCCACA G t *A* (SEQ ID NO: 10) |
| G-gJAK2-(-1)LNA-R | LNA at -1 and -1 Mismatch | TTTACTTACTCTCGTCTCCACA G *t* C (SEQ ID NO: 11) |
| T-gJAK2-(-1)LNA-R | LNA at -1 and -1 Mismatch | TTTACTTACTCTCGTCTCCACA G *t* A (SEQ ID NO: 12) |
| G-gJAK2-(-2)LNA-R | LNA at -2 and -1 Mismatch | TTTACTTACTCTCGTCTCCACA *G* t C (SEQ ID NO: 13) |
| T-gJAK2-(-2)LNA-R | LNA at -2 and -1 Mismatch | TTTACTTACTCTCGTCTCCACA *G* t A (SEQ ID NO: 14) |
| G-gJAK2-(-3)LNA-R | LNA at -3 and -1 Mismatch | TTTACTTACTCTCGTCTCCAC *A*G t C (SEQ ID NO: 15) |
| T-gJAK2-(-3)LNA-R | LNA at -3 and -1 Mismatch | TTTACTTACTCTCGTCTCCAC*A* G t A (SEQ ID NO: 16) |
| G-gJAK2-(-4)LNA-R | LNA at -4 and -1 Mismatch | TTTACTTACTCTCGTCTCC*A*C AG t C (SEQ ID NO: 17) |
| T-gJAK2-(-4)LNA-R | LNA at -4 and -1 Mismatch | TTTACTTACTCTCGTCTCC*A*C AG t A (SEQ ID NO: 18) |

[A] Allele specific primers are named beginning with uppercase G or T based on the sequence of the sense strand. The G-primers are specific for the wild-type allele, while, the T-primers are specific for the mutant allele.
[B] LNA bases are depicted in uppercase italics, bolded and underlined; while, the mismatches are highlighted in bold lowercase. Base positions are counted beginning at the 3' end of the primers.

Pyrosequencing. Quantitation of the JAK2 mutant allele was done as previously described (16) using a PSQ HS 96 pyrosequencer and reagents provided by the manufacturer (Biotage, Uppsala, Sweden).

Allele frequency calculations. Allele frequency was calculated as described by Germer, et. al. (12). The difference in cycle threshold ($\Delta C_t$) between the two matched and mismatched allele-specific PCR reactions is a measure of the proportion or frequency of the allele assuming that initial replication efficiency is 100%. If the amplification efficiencies of the two allele-specific reactions differ slightly, this can be corrected by measuring the $\Delta C_t$ on a DNA sample known to be heterozygous for the mutation of interest. The $\Delta C_t$ in the heterozygous sample should be zero, any deviation from zero can be subtracted from all $\Delta C_t$ measurements in order to compensate for differing amplification efficiencies and is represented by HC (heterozygote correction factor). Therefore, HC $\Delta C_t$ represents the heterozygote corrected difference in cycle threshold between the two allele-specific PCR reactions.

$$\Delta C_t = C_t\text{allele}_1 - C_t\text{allele}_2 \qquad (1)$$

and $$HC\Delta C_t = \Delta C_t - (HCC_t\text{allele}_1 - HCC_t\text{allele}) \qquad (2)$$

Results obtained in equations 1 and 2 are used to find the frequency of allele$_1$ in equation 3:

$$\text{Freq·allele}_1 = 1/(E^{HC\Delta C_t} + 1) \qquad (3)$$

where E represents the efficiency of PCR amplification for allele$_s$ and can be deduced by the slope of serially diluted sample.

Statistical calculations. One-way ANOVA and multiple comparison (Newman-Keuls test) were used to analyze statistically significant differences between ΔCt and delay results (FIG. 3) when comparing primer design modifications. Statistical significance was assumed for P<0.05.

Results

Assay Design. Allele-specific PCR is widely used for SNP genotyping and is based on amplification of DNA by an allele-specific primer matching the polymorphism at the 3' terminal position. In theory, the allele-specific primer containing the mismatched nucleoside at the 3' end should not be extended by Taq DNA polymerase (Taq). However, it has been shown that Taq can extend mismatched allele-specific primers, generating false-positive results. A number of different strategies have been developed to improve specificity and reliability of this technique (14, 17-20).

The methods of the present invention combine two different strategies in a novel approach: by including a second mismatch and a modified LNA base. It is hypothesized that inclusion of a second mismatch at the −1 position further destabilizes the 3' end of the allele-specific mismatched primer, resulting in an increase in specificity of the matched primer after the first cycle of PCR. Oligonucleotides carrying LNA bases are thought to favor the formation of A-helix DNA duplexes, improved base-pair stacking and higher melting temperature (Tm) (15). It is further hypothesized that the LNA at the −2 position stabilizes the matched bases of the allele-specific primers of the invention and stabilizes the 3' end, thereby increasing primer Tm, which enhances allele specific amplification, and decreases assay to assay variability. A schematic representation of this assay design is provided in FIG. 1.

Figure 2:
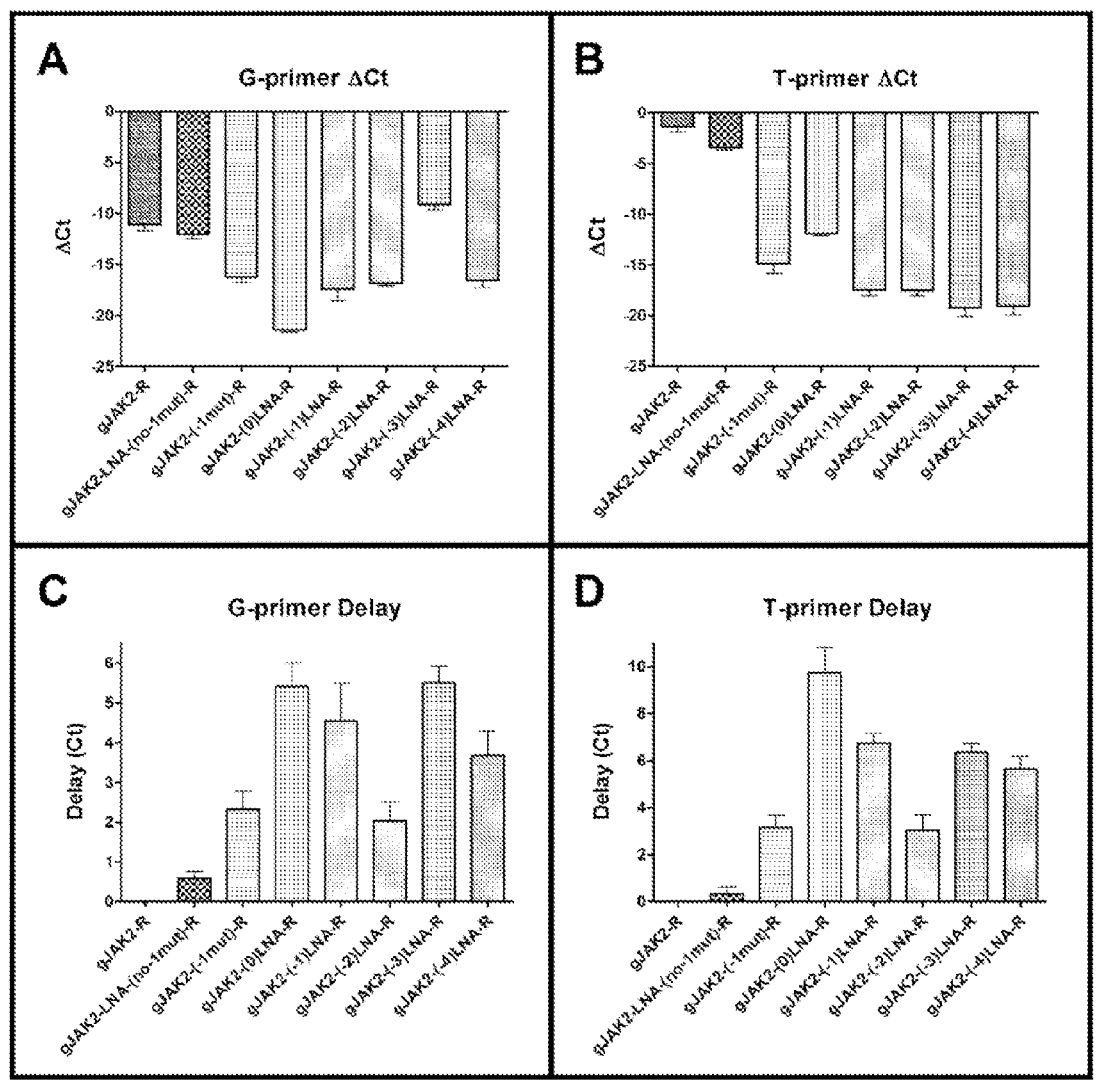
FIG. 2 shows bar graphs comparing primer modifications for discrimination of wild-type and mutant JAK2$^{V617F}$ alleles. Genomic DNA from a healthy donor (JAK2 homozygous wild-type) and a PV patient (JAK2 homozygous mutant) were used to evaluate the performance of G and T allele specific primers bearing different permutations of mismatch and LNA modifications, and with no modifications (see supplemental Table S1). (A) ΔCt for G-allele specific primers, more negative indicates greater discrimination. (B) ΔCt for T-allele specific primers, more negative indicates greater discrimination. (C) Ct delay resulting from introduction of modification in G-allele specific primers compared to G-primer without modification. (D) Ct delay resulting from introduction of modification in T-allele specific primers compared to T-primer without modification. Data represent mean±SD of three independent determinations.

Real-Time AS-PCR. Genomic DNA was isolated from granulocytes of a control (Ctl) and one PV patient (PV4) representing the two homozygous JAK2 genotypes (GG and TT) as previously determined by pyrosequencing. Comparison of our novel allele-specific primer design, with control allele-specific primers bearing a mismatch, LNA modified base, and no modification (Table 1) was evaluated by real-time PCR using both homozygous genotypes (FIG. 2). A dynamic increase in fluorescence, reflecting probe cleavage, was seen with all primer designs. In the absence of any modification, the G-allele-specific primer efficiently extended both matched and mismatched targets resulting in poor discrimination between genotypes (FIG. 2A). Allele-specific primers carrying the LNA modified base showed only marginal improvement discriminating between genotypes (FIGS. 2A and 2B). Results for the primers carrying the LNA and extra base mismatch (FIGS. 2A and 2B) were excellent for both wild-type and mutant homozygous genotypes, with ΔCt greater than 14 cycles between matched and mismatched allele-specific primers. This indicated that the additional mismatch was responsible for improved discrimination compared to allele-specific primers bearing no modifications.

Next the reproducibility of the results was examined by determining the ΔCt of matched and mismatched primers in three independent measurements (FIGS. 2A and 2B). Results indicate that, although discrimination is significantly improved by the introduction of the mismatch at the −1 position, addition of the LNA base at the −2 position enhances reproducibility. It was also found that positioning of the LNA base at either the −1 or −4 positions slightly improved discrimination, albeit at a cost of decreasing the sensitivity of the assay (FIGS. 2C and 2D). ΔCt differences obtained for the G-allele specific primers, bearing either the mismatch alone (gJAK2-(−1mut)-R) or mismatch and −2 LNA (gJAK2-(−2)LNA-R) modifications, were not significant (P>0.05). In contrast, the differences in ΔCt for the T-allele specific primers, harboring the same modifications as above, were significant (P<0.05).

Serial dilutions of genomic DNA from both wild-type and mutant homozygous samples were assayed by real-time PCR using the allele-specific primers of the present invention. PCR reaction efficiency was determined for both allele-specific primers and was found is to be greater than 92%. Allele detection limits were estimated to be in the range of 50 pg genomic DNA (approximately 7 diploid genome equivalents). Since JAK2$^{V617F}$ is a somatic mutation, the unequal amplification efficiency was determined and the heterozygosity correction factor (HC) between the allele-specific primers calculated by measuring the ΔCt of a 50:50 mix of wild-type and homozygous mutant DNA samples.

Real-time vs. pyrosequencing. Since pyrosequencing is considered a quantitative and reliable technique for the detection of SNP, a blind comparison was performed between the allele frequency determinations and those independently obtained by pyrosequencing. Table 2 shows the estimated frequencies of the mutant T-allele in granulocytes isolated from different PV patients obtained by both real-time PCR and pyrosequencing with an excellent correlation in a linear regression model (y=1.01x+2.6; $R^2$=0.99; P<0.0001).

TABLE 2

Comparison of JAK 2 T allele frequency obtained by pyrosequencing and method of invention.

| Patient Number | Sample Date | T-Allele (%) (Pyrosequencing) | T-allele (%) (AS-PCR) |
| --- | --- | --- | --- |
| PV1 | Nov. 3, 2005 | 57.0 | 64.8 |
| PV2 | Mar. 1, 2005 | 78.3 | 80.7 |
| PV3 | Apr. 13, 2005 | 21.3 | 23.4 |
| PV3 | Jun. 30, 2005 | 28.7 | 30 |
| PV4 | Dec. 29, 2004 | 69.4 | 66.4 |
| PV4 | Mar. 1, 2005 | 59.2 | 60.4 |
| PV4 | May 26, 2005 | 57.9 | 68.4 |
| PV4 | Jun. 30, 2005 | 18.8 | 24.1 |
| PV5 | Aug. 2, 2005 | 44.9 | 46.6 |
| PV6 | Aug. 31, 2005 | 0.0 | 0.0 |
| PV7 | Jan. 4, 2005 | 84.1 | 88.5 |
| PV7 | Mar. 30, 2005 | 66.7 | 73.4 |
| PV7 | Jun. 30, 2005 | 80.2 | 82.2 |
| PV7 | Jul. 12, 2005 | 78.4 | 84.1 |
| PV7 | Oct. 14, 2005 | 79.0 | 81.4 |
| PV8 | Oct. 19, 2005 | 96.0 | 97.0 |
| PV9 | Aug. 22, 2005 | 83.0 | 87.3 |
| PV10 | May 11, 2005 | 80 | 84.2 |

Reproducibility of the assay. In order to test the robustness of this design, the frequency of the JAK2 mutant T-allele was determined in 31 genomic DNA samples from peripheral blood and granulocytes of PV patients (Table 3). Three independent measurements were performed for each sample. Mean allele frequency was found to deviate by less than 1.5%, on average, for all samples tested (Table 3).

TABLE 3

Reproducibility as estimated by three independent measurements.

| Patient Number | Date | % T-allele (PB-DNA) | % T-allele (GNC-DNA) |
| --- | --- | --- | --- |
| PV3 | Apr. 13, 2005 | 16.4 (±0.8) | 23.4 |
| PV4 | Mar. 1, 2005 | 38.8 (±3.0) | 60.4 |
| PV4 | Jun. 30, 2005 | 16.8 (±0.9) | 27.2 (±4.7) |
| PV4 | Dec. 27, 2005 | 41.1 (±2.8) | 55.1 (±2.0) |
| PV6 | Aug. 31, 2005 | N.D. | 0.0 (±0.0) |
| PV7 | Jan. 4, 2005 | 74.8 (±1.0) | 88.2 (±0.7) |

TABLE 3-continued

Reproducibility as estimated by three independent measurements.

| Patient Number | Date | % T-allele (PB-DNA) | % T-allele (GNC-DNA) |
|---|---|---|---|
| PV7 | Jul. 12, 2005 | 74.6 (±0.6) | 84.8 (±1.6) |
| PV7 | Oct. 14, 2005 | 67.3 (±4.4) | 82.2 (±1.6) |
| PV8 | Oct. 19, 2005 | 89.7 (±0.3) | 97.4 (±0.5) |
| PV10 | May 11, 2005 | 63.4 (±1.3) | 84.2 (±1.0) |
| PV12 | Sep. 3, 2005 | 27.3 (±1.9) | 40.7 (±1.0) |
| PV14 | Nov. 30, 2005 | 74.7 (±2.0) | 78.1 (±1.1) |
| PV15 | Nov. 8, 2005 | 0.1 (±0.0) | 0.0 (±0.1) |
| PV17 | Dec. 8, 2005 | 37.1 (±0.4) | 44.9 (±1.3) |
| PV18 | Nov. 8, 2005 | 85.8 (±0.8) | 91.4 (±0.3) |
| PV19 | Nov. 15, 2005 | 66.5 (±0.7) | 92.5 (±4.9) |
| PV21 | Mar. 15, 2005 | 95.8 (±0.4) | 99.9 (±0.0) |

Figure 3:
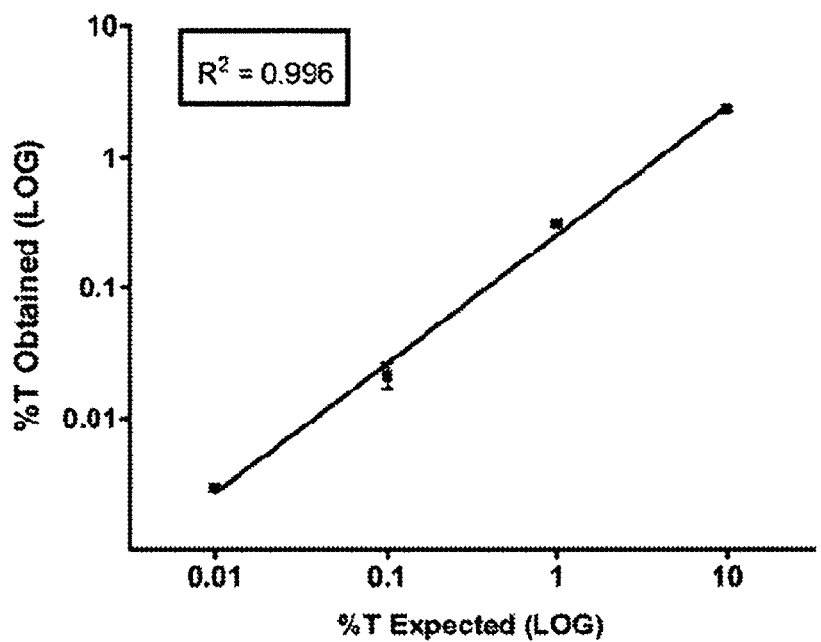
FIG. 3 shows a graph charting the limit of mutant allele detection in the presence of a large excess of wild-type allele. Genomic DNA from HEL cells (JAK2 homozygous mutant) was mixed in decreasing proportions to DNA from a healthy donor (JAK2 homozygous wild-type). Ensuing mixtures containing 10, 1, 0.1 and 0.01% HEL gDNA were used to determine JAK2$^{V617F}$ mutant allele frequency. Linear regression of kinetic AS-PCR determinations vs. expected allele frequencies showed excellent correlation ($R^2$=0.996; P<0.002). Data represent mean±SD of three independent determinations.

T-allele frequency (%) was determined for peripheral blood genomic DNA (PB-DNA) and for granulocyte genomic DNA (GNC-DNA). Results are shown as the mean with standard deviation in between parenthesis. N.D. = Not Determined Mutant allele frequency sensitivity. The JAK2 mutant allele detection sensitivity was investigated by mixing normal control genomic DNA with decreasing proportions of genomic DNA isolated from the human erythro-leukemic cell line (HEL), which is homozygous for the JAK2$^{V617F}$ mutation (FIG. 3). The most sensitive techniques used to detect low levels of SNP are still limited by the mass of gDNA assayed. The mass of a single haploid human genome is estimated to be 3.7 pg. Therefore, if 40 ng of genomic DNA are used to assay for the presence of a mutated allele with a frequency of 0.01%, only a single copy may be detected by random chance. Most assays use 20-50 ng gDNA, hence, a reasonable detection limit should be 0.1%. The presence of the JAK2 mutant allele was reliably detected at a frequency of 0.1% using 40-50 ng gDNA (FIG. 3). However, if gDNA exceeding 400 ng were used, mutant allele frequencies below 0.01% may be reliably detected (FIG. 3).

Is JAK2$^{V617F}$ the disease initiating mutation? The relevance and usefulness of the primer design of the present invention has been demonstrated while investigating mutant JAK2 T-allele frequency and clonality in several female PV patients. Genomic DNA isolated from granulocytes of 10 female PV patients, who were found to be clonal by the X-chromosome transcriptional clonality assay (21), were used for the determination of JAK2 mutant allele frequency. In 3 of the 10 female patients with clonal granulopoiesis, mutant allele frequencies were below 50% (27.5±11) while the remaining 7 had frequencies greater than 50% (75±10.5). This result, in combination with the clonality data, is indicative of a heterogeneous population composed of granulocytes with differing JAK2$^{V617F}$ genotypes (GG, GT or TT) and reinforces the model wherein the mutation is not the disease initiating event.

Figure 4:
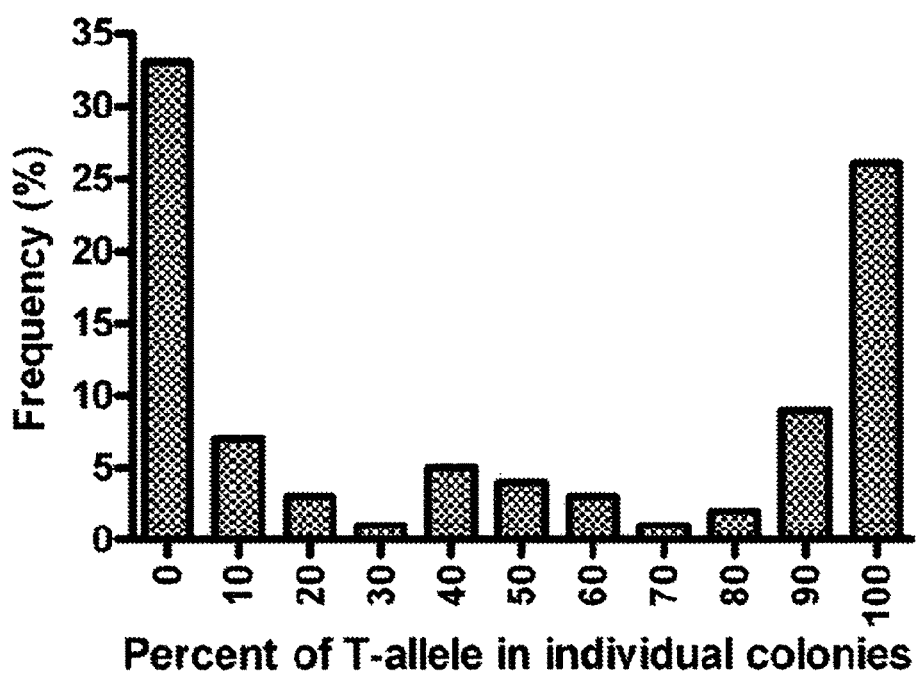
FIG. 4 is a chart showing the BFU-E colony analysis showing a trimodal distribution of T-allele frequencies. Frequency distribution of all BFU-E colonies picked and used for genotyping the JAK2$^{V617F}$ mutation, as described in the examples, below. The cutoffs used for defining genotypes are indicated in Table 3.

Direct evidence for JAK2$^{V617F}$ as a secondary event. Since erythropoietin independent growth of BFU-E colonies (also known as EEC) is considered a hallmark of PV (22), the methods of the invention were used to determine the JAK2 mutant T-allele frequency in single colonies. In preliminary experiments using JAK2 sequencing and allele discrimination real-time PCR, it was found that a majority of untreated PV patients, and patients stable on their respective therapies, had erythropoietin independent BFU-E that were homozygous for the JAK2$^{V617F}$ mutation. Nevertheless, some colonies were heterozygous, while rare colonies had a wild type JAK2 genotype. Using the novel and more sensitive quantitative assay described herein, this issue was reexamined. Since individual EEC colonies represent the "clonal" growth and proliferation initiated by a single affected cell (23), allele frequencies should reflect those normally observed for any germline SNP (0, 50, and 100). Mononuclear cells from two female and two male PV patients were used to grow and harvest 89 individual BFU-E colonies (24), a total of 69 genotypes were determined (Table 4). Deviation from the expected allele frequency was small, and was due to contamination by other colonies or cells picked together while harvesting the colony of interest. Colonies with allele frequency deviations greater than 10% as determined by the JAK2 mutant T-allele frequency distribution (FIG. 4), were discarded in order to avoid any bias during genotyping (Table 4). Both heterozygous and homozygous (mutant and wild-type) JAK2$^{V617F}$ colonies were detected (Table 4).

TABLE 4

JAK2$^{V617F}$ allele frequency in isolated BFU-E colonies.

| Patient Number | T-allele (%) in GNC | BFU-E with 0U Epo | | | BFU-E with 3U Epo | | |
|---|---|---|---|---|---|---|---|
| | | G/G | G/T | T/T | G/G | G/T | T/T |
| PV18 | 91.4 | 0 | 0 | 7 | 2 | 1 | 8 |
| PV22 | N.D. | 1 | 1 | 3 | 5 | 0 | 7 |
| PV23 | 20 | 6 | 1 | 0 | 7 | 4 | 0 |
| PV24 | 89 | 1 | 2 | 2 | 6 | 0 | 4 |
| Total Colonies | | 8 | 4 | 12 | 20 | 5 | 19 |

Genotypes represent the quantitative determination of the frequency of mutant allele with cutoffs as follows:
G/G (0-10%);
G/T (40-60%); and
T/T (90-100%).
Colonies that are not within these set cutoffs are deemed contaminated by other cells while harvesting and are discarded.
N.D. = Not Determined The clinical significance and role of the JAK2 mutation in the pathology and progression of disease, especially for PV, is being investigated. It appears that some complications of MPDs, including the degree of marrow fibrosis, correlate with the overall proportion of the mutant allele in circulating cells. The high frequency of JAK2$^{V617F}$ in PV makes this an excellent disease marker. Hence, disease progression, treatment, and development of novel chemotherapeutics for PV can be assessed by following changes in the proportion of mutant JAK2 allele in clonal blood granulocytes.

AS-PCR allows determination of the allele frequency of any polymorphism or mutation based on the difference in the number of PCR cycles needed to generate detectable product. AS-PCR can also be a valuable tool to determine the frequency of rare alleles when somatic mutations are present in a small percentage of cells within a tissue sample. Addition of mismatches in a primer requires careful design, strand selection, and optimization of the many variables that affect primer stability and target amplification. Furthermore, the use of LNA in the design of oligonucleotide primers and probes, resulted in improved specificity and allele discrimination compared to unmodified primers (20, 25). However, the synergistic effect, as shown here, of primers harboring a mismatched nucleoside and LNA modification in AS-PCR has not been investigated.

As demonstrated herein, AS-PCR may be used for quantitation of somatic mutations using the novel primer design of the present invention, providing sensitive, accurate, and highly reproducible results. Independent investigators have tested this design in different laboratories using two kinetic PCR platforms (ABI-7000 made by Applied Biosystems Foster City, Calif., and a Light Cycler made by Roche Applied Science, Indianapolis, Ind.). Results for the samples tested were nearly identical between platforms, and comparable to previous estimates of allele frequency obtained by pyrosequencing (results not shown). Further, amplicon detection during kinetic AS-PCR can be done using any available technology, (e.g. SYBR-Green, TaqMan Probe, Molecular Beacon, Hybridization Probe) at the discretion and convenience of the investigator.

Preliminary results have been obtained for the quantitation of expressed mutant allele frequency in mRNA of PV patients. This primer design strategy can also be applied to determine allelic frequencies of other SNP or mutations. For example, this approach may be used to detect expressed X-chromosome SNP, subjected to inactivation in women, for determination of clonality (21). Preliminary results indicate that allele-specific primers designed, using the invention described herein, for quantitation of 5 different expressed X-chromosome SNPs, used for determination of clonality in women, work flawlessly with minimal optimization required.

Potential applications for our primer design are varied, such as, quantitative determination of mosaicism; proportion of fetal cells in maternal circulation; detection of minimal residual disease associated with known somatic mutation (such as reduction of malignant cells by chemotherapy or reappearance of resistant clone); rapid monitoring of efficacy of new drugs in both "in vitro" systems, as well as clinical trials, and many others that require quantitation of allele frequencies.

The quantitative AS-PCR assay described herein elucidates the order of genetic events leading to the $JAK2^{V617F}$ mutation in the ontogeny of clonal hematopoiesis in PV. In contrast to a recent study reporting the absence of $JAK2^{V617F}$ negative Epo independent BFU-E colonies (26), such colonies were found in samples from PV patients. A possible explanation for this discrepancy may relate to the sensitivity and methods used for detection of the mutant allele. The determination of zygosity in granulocytes from PV patients by Scott and colleagues was done in samples that were collected at least 6 months prior to the samples used for clonogenic assay (26). It has also been found that X-chromosome based methylation clonality assays have significant shortcomings compared to transcriptional based X-chromosome clonality assays (26). In addition, Scott and colleagues used a qualitative PCR and restriction endonuclease digestion assay for the genotyping of their samples, and hence, could not distinguish colonies potentially contaminated with other cells (26). In this assay, identification of JAK2 wild-type genotypes, requires the PCR product to be fully digested by BsaXI. Therefore, homozygous JAK2 mutant allele and heterozygous colonies may be erroneously genotyped due to incomplete digestion. Since the present methods make use of real-time monitoring during PCR amplification, and the data generated is quantitative, genotyping determinations can be made with greater confidence. Further, the in vitro analysis of BFU-E response to erythropoietin (clonogenic assay) is laborious and data not always easy to interpret; however, this assay has been developed and have routinely used it since 1974 (22). The reproducibility and use of the clonogenic assay has been validated in our studies of a large number of congenital and acquired polycythemic states such as primary familial and congenital polycythemia and Chuvash polycythemia (27).

The presence of wild-type JAK2 Epo independent colonies suggests the existence of a distinct, and as of now, unknown alternative mechanism active in erythropoiesis/hematopoiesis. Moreover, these results indicate the presence of an undefined molecular lesion that precedes the $JAK2^{V617F}$ mutation. Finally, this data suggest that development of chemotherapeutics that target the $JAK2^{V617F}$ clonal cells may not suffice to cure PV.

Example 2

Analysis of Mutant cMPL in Philadelphia Chromosome-Negative Myeloproliferative Disorders (Ph⁻MPDs)

cMPL is a gene encoding the thrombopoietin receptor, which is essential for thrombopoiesis and contributes to pluripotent hematopoietic stem cell expansion. A gain of function cMPL mutation, MPLW515L, was identified in myeloid cells from patients with primary myelofibrosis (PMF). Subsequent studies identified a second gain of function mutation, MPLW515K, in PMF and essential thrombocytosis (ET). Mutation W515L results in a TGG→TTG conversion in W515L. Mutation W515K results in a TGG→AAG conversion in W515K.

A rapid, sensitive, quantitative real time PCR assay was developed that enhanced cMPL allelic discrimination, utilizing a primer that included a mismatch in the −2 position, and a locked nucleic acid nucleoside at the −3 position of the allele-specific primers. Genomic DNA from peripheral blood granulocytes of 197 MPD patients was analyzed. It was found that 10/197 (5.1%) carried one of the two cMPL mutations. Further, 5 of these patients were also JAK2V617F positive. cMPL mutations were detected in 1/78 (1.3%) PV patients, 3/56 (5.4%) ET patients, 4/49 (8.2%) PMF patients, and 2/11 (18%) MPD-unspecified patients. W515L accounted for 9/10 cases, with W515K accounting for only 1. Of the ten positive samples, five (including the patient with PV) had ≤1% mutant alleles.

To confirm the validity of this assay, DNA from 96 normal controls was tested. Neither W515L nor W515K was detected (p=0.03 compared to samples from the Ph⁻MPD patients). Additionally, when DNA from megakaryocytic colonies from a patient with 0.70% mutant alleles was analyzed, 12.5% of colonies were found to be heterozygous for cMPLW515L. Results were similar for both thrombopoietin-dependent and thrombopoietin-independent colonies.

TABLE 5

Primer and Probe Sequences for Determination of cMPL Alleles.

| Primer/Probe | Sequence 5' to 3' | |
|---|---|---|
| cMPL-R (W515L) | GGGTCACAGAGCGAACCA | (SEQ ID NO: 19) |
| cMPL-LNA-G-F | GCCTGCTGCTGCTGA*G*cTG | (SEQ ID NO: 20) |
| cMPL-LNA-A-F | GCCTGCTGCTGCTGA*G*cTT | (SEQ ID NO: 21) |
| cMPL-R (W515K) | GGGTCACAGAGCGAACCA | (SEQ ID NO: 22) |
| cMPL-LNA-TG-F | GCCTGCTGGTGCTGA*G*cT | (SEQ ID NO: 23) |
| cMPL-LNA-AA-F | GCCTGCTGCTGCTGA*G*cA | (SEQ ID NO: 24) |

Genomic DNA was isolated from peripheral blood granulocytes. Real time AS-PCR was performed on an Applied Biosystems 7500 Sequence Detection System (Applied Biosystems, Foster City, Calif., USA). Typical reactions (15 ul) consisted of 1× TaqMan Universal PCR master mix (Applied Biosystem); Enzyme activation (95° C. for 10 minutes) was followed by 45 cycles of 95° C. for 15 seconds, and 60° C. for 1 minute.

Typical reactions (15 ul) consisted of 1× TaqMan Universal PCR master mix (Applied Biosystem); 300 nM universal reversed primer and allele-specific forward primers; 125 nM FAM-labeled cMPL-MGBNFQ probe (Applied Biosystems), (Shown in Table 1); and ing to 50 ng of gDNA. Allele-specific primers were designed using the software program Oligo 6.7 (Molecular Biology Insights, Inc., Cascade, Colo., USA) and synthesized by IDT (Integrated Technologies, Coralville, Iowa, USA).

TABLE 6

Comparison of T-allele frequency for W515L mutation and A-allele frequency for W515K mutation obtained by pyrosequencing and our method.

| Patient number | Pyrosequencing | | AS-PCR | |
|---|---|---|---|---|
| | W515L T-allele (%) | W515K A-allele (%) | W515L T-allele (%) | W515K A-allele (%) |
| 1 | 0 | 67 | 0 | 69 |
| 2 | 0 | 0 | 1 | 0 |
| 3 | 11 | 0 | 13 | 0 |
| 4 | 0 | 0 | 32.8 | 0 |
| 5 | 0 | 0 | 1 | 0 |
| 6 | 0 | 0 | 0.8 | 0 |
| 7 | 0 | 0 | 1 | 0 |
| 8 | 0 | 0 | 0.8 | 0 |
| 9 | 0 | 0 | 1 | 0 |
| 10 | 0 | 0 | 1 | 0 |
| 11 | 0 | 0 | 0.7 | 0 |
| 12 | 0 | 0 | 1 | 0 |
| 13 | — | — | 10.3 | 0 |
| 14 | — | — | 53.5 | 0 |
| 15 | 1 | 0 | 0 | 0 |
| 16 | 1 | 0 | 0 | 0 |
| 17 | 3 | 0 | 0 | 0 |
| 18 | 3 | 0 | 0 | 0 |
| 19 | 2 | 0 | 0 | 0 |
| 20 | 2 | 0 | 0 | 0 |
| 21 | 3 | 0 | 0 | 0 |
| 22 | 4 | 0 | 0 | 0 |
| 23 | 2 | 0 | 0 | 0 |
| 24 | 1 | 0 | 0 | 0 |
| 25 | 1 | 0 | 0 | 0 |

Results

DNA was analyzed from peripheral blood granulocytes of 197 patients and found that 10/197 (5.1%) carried one of the two cMPL mutations and that 5 of these patients were also JAK2V617F positive. By diagnosis, 1/78 (1.3%) PV patients, 3/56 (5.4%) ET patients, 4/49 (8.2%) PMF patients and 2/11 (18%) MPD-Unspecified patients were affected. W515L accounted for 9/10 cases with W515K accounting for 1 of the 10 cases. Of the ten positive samples, five (including the patient with PV) had ≤1% mutant alleles. To confirm the validity of our assay, DNA was tested from 96 normal controls. Neither W515L nor W515K was detected (p=0.03 compared to samples from the Ph⁻MPD patients). When DNA from thrombopoietin-independent and -dependent megakaryocyte colonies from a patient with 0.70% mutant alleles was analyzed, 12% were found to be heterozygous for cMPLW515L.

These studies demonstrate the sensitivity and accuracy of this assay and show that cMPL activating mutations are more common in ET than previously reported. Mutant allele frequency appears greater in megakaryocytic cultures, perhaps indicating a proliferative advantage for the cMPL-mutant clone. That mutant cMPL and JAK2V617F can be found in the same patient demonstrates the molecular heterogeneity of Ph⁻MPDs and emphasizes the need for prospective studies designed to determine the relationship between genotype and clinical phenotype.

Example 3

Quantitative Real Time PCR Assays to Determine Clonality of Hematopoiesis

Methods for determining phenotypic clonality rely on the principle of X chromosome inactivation (XCIP), unique to women, and are based on differentiating transcriptionally active X-chromosomal genes from inactive X-chromosomal genes.

Clonality studies were performed using BTK, FHL1, IDS, G6PD and MPP1 exonic polymorphisms. Genomic DNA was used for genotyping exonic polymorphisms, using TaqMan allelic-discrimination assays. Genomic DNA and total RNA were isolated from peripheral blood granulocytes and platelets.

Real time AS-PCR was performed on an Applied Biosystems 7500 Sequence Detection System (Applied Biosystems, Foster City, Calif., USA). Typical reactions (15 ul) consisted of 1× TaqMan Universal PCR master mix (Applied Biosystem); 20× TaqMan SNP Genotyping Assay Mix (Applied Biosystems); and 1-20 ng of purified genomic DNA. Enzyme activation (95° C. for 10 minutes) was followed by 45 cycles of 92° C. for 15 seconds, and 60° C. for 1 minute.

The transcriptional clonality assay (TCA) was performed using total RNA. cDNA templates for real time AS-PCR were prepared by the reverse transcriptase PCR from total cellular RNA using 50 ng of mRNA and SuperScript III First-Strand Synthesis SuperMix for qRT-PCR (Invitrogen). Allele-specific primers were designed for exonic polymorphisms in the BTK, FHL1, IDS, G6PD and MPP1 genes in accordance with the disclosed invention, including a mismatch in the −1 position, and a locked nucleic acid nucleoside at the −2 position. Primers were used in quantitative real time PCR assays to determine clonality of hematopoiesis in older female subjects.

Typical reactions (15 ul) consisted of 1× TaqMan Universal PCR master mix (Applied Biosystem); 300 nM universal and allele-specific forward or reversed primers; 125 nM FAM-labeled marker-MGBNFQ probe (Applied Biosystems), (Shown in Table 1); and 2 µl of cDNA. Allele-specific primers were designed using the software program Oligo 6.7 (Molecular Biology Insights, Inc., Cascade, Colo., USA) and synthesized by IDT (Integrated Technologies, Coralville, Iowa, USA).

TABLE 7

Primer and Probe sequences for Clonality Analysis of Hematopoesis

| Primer/Probe | Sequence 5' to 3' |
|---|---|
| FAM-AS-MPP1-MGB | 6FAM-ACAGTCCTGTACGGTGG-MGBNFQ (SEQ ID NO: 25) |
| cMPP1-R | GGAGCCTTGTCTATGGATCATGC (SEQ ID NO: 26) |
| cMPP1-LNA-G-F | CACAGAAGAGCCCATAGGAATCAgG (SEQ ID NO: 27) |
| cMPP1-LNA-T-F | CACAGAAGAGCCCATAGGAATCAgT (SEQ ID NO: 28) |

TABLE 7-continued

Primer and Probe sequences for Clonality Analysis of Hematopoesis

| Primer/Probe | Sequence 5' to 3' |
|---|---|
| FAM-AS-FHL1-MGB | 6FAM-TGCAGGAACATCTGAGG-MGBNFQ (SEQ ID NO: 29) |
| cFHL1-F | TTTATGGGTTTGGAAACTTGCAT (SEQ ID NO: 30) |
| cFHL1-LNA-G-R | CTAGAGTTTTGCGGTTACTTgC (SEQ ID NO: 31) |
| cFHL1-LNA-T-R | CTAGAGTTTTGCGGTTACTTgT (SEQ ID NO: 32) |
| FAM-AS-IDS-MGB | 6FAM-CCTTCCTCTGAGAAGTAT-MGBNFQ (SEQ ID NO: 33) |
| cIDS-R | CCTCGACATGTCTTAGTGTTT (SEQ ID NO: 34) |
| cIDS-LNA-C-F | TGGGATATCTTCTAACCATAgC (SEQ ID NO: 35) |
| cIDS-LNA-T-F | TGGGATATCTTCTAACCATAgT (SEQ ID NO: 36) |
| FAM-AS-G6PD-MGB | 6FAM-AGCGCCTCATCCTG-MGBNFQ (SEQ ID NO: 37) |
| cG6PD-R | CAGTGGGGTGAAAATACGC (SEQ ID NO: 38) |
| cG6PD-LNA-C-F | AGCTCCCTGACGCCTtC (SEQ ID NO: 39) |
| cG6PD-LNA-T-F | AGCTCCCTGACGCCTtT (SEQ ID NO: 40) |
| FAM-AS-BTK-MGB | 6FAM-TACCTTCTCTGAAGCCAG-MGBNFQ (SEQ ID NO: 41) |
| cBTK-F | GAGACTGCTGAACACATTGC (SEQ ID NO: 42) |
| cBTK-LNA-C-R | CATCTGCTTTCTCATGCCtC (SEQ ID NO: 43) |
| cBTK-LNA-T-R | CATCTGCTTTCTCATGCCtA (SEQ ID NO: 44) |

Results

Using our novel quantitative real time PCR assay, 26 healthy females were tested. Subjects were ≥65 years of age with no history of malignant disorders, unexplained anemia, or autoimmune disorder. Neither clonal XCIP, nor extreme skewing of XCIP was noted in any of the study subjects. Representative real time PCR results are shown in Table 2.

TABLE 8

Exonic Polymorphism genotypes and allelic frequencies in healthy females ≥65 years of age

| | Exonic Polymorphism genotypes | | | | | Exonic Polymorphism Allelic Frequencies | | | | |
|---|---|---|---|---|---|---|---|---|---|---|
| | | | | | | MPP1 | FHL1 | IDS | G6PD | BTK |
| Samples | MPP1 | FHL1 | IDS | G6PD | BTK | G/T | G/T | C/T | C/T | C/T |
| GC1 | + | | | | | 54 46 | | | | |
| GC2 | | + | | | | | 61 39 | | | |
| GC3 | | + | | | | | 63 37 | | | |
| GC4 | | + | | + | | | 56 44 | | | 58 42 |
| GC5 | | + | + | | | | 53 47 | 53 47 | | |
| GC6 | | | + | | | | | 40 60 | | |
| GC7 | | | + | | | | | 63 37 | | |
| GC8 | | + | | | | | 34 66 | | | |
| GC9 | | + | | | | | 61 39 | | | |
| GC10 | + | | | | | 74 26 | | | | |
| GC11 | | + | | + | | | | 34 66 | | 32 68 |
| GC12 | + | | + | | | | | | | |
| GC13 | | + | + | | | | 42 58 | 41 59 | | |
| GC14 | + | | + | | | 59 41 | | 52 48 | | |
| GC15 | | + | + | | | | 43 57 | 54 46 | | |
| GC16 | | + | | + | | 73 27 | 30 70 | | | 31 69 |
| GC17 | | − | − | | | | | | | |
| GC18 | | − | − | | | | | | | |
| GC19 | | − | − | − | − | | | | | |
| GC20 | | | + | + | | | | 70 30 | | 32 68 |
| GC21 | | | + | | | | | 48 52 | | |
| GC24 | | + | | | | | 64 35 | | | |
| CH2 | + | | + | + | | 23 77 | | 36 64 | 61 39 | |
| CH3 | + | | | + | | 48 52 | | | 26 74 | |
| CH4 | | | | + | | | | | 60 40 | |
| CH5 | + | + | + | | | 64 36 | 30 70 | 65 35 | | |

Example 4

The methods and compositions of the present invention were also used to determine different levels of Spectrin allele transcripts for a novel mutation in exon 2, codon 34: CGG→CCG (Arg>Pro).

Mutations of spectrin (Sp) involving the Sp heterodimer self-association site (the I domain of Sp) represent the most common group of membrane skeletal defects in hereditary elliptocytosis (HE) and a closely related disorder, hereditary pyropoikilocytosis (HPP). HPP is characterized by extreme anisocytic microcytosis, a severe spectrin dimer self-association defect and spectrin deficiency. The conventional explanation for the different phenotypes is that HPP subjects are compound heterozygotes for a Sp defect that interferes with Sp tetramer assembly and a second defect which results in decreased synthesis of functional Sp.

In contrast, HE subjects have normal spectrin content and a less severe sp self-association defect. The clinical expression of HE/HPP is influenced by the inheritance of modifying factors such as the Sp hypomorphic mutation, LELY. LELY is a low expression allele of the Sp gene characterized by a C>G mutation in codon 1857 of exon 40 and a C>T-12 mutation in intron 45 that is responsible for partial skipping of exon 46, which is essential for the functional assembly of /b sp dimers.

Here we describe a family of northern European descent in which members had different erythrocyte morphologies ranging from atypical HPP to HE to normal and a novel Sp mutation. Quantitation of RBC membrane proteins of the propositus with atypical non-microcytic HPP revealed 48% spectrin dimers (control 10%) due to a marked increase in the 74 kD I Sp peptide. There was only a slight decrease in the spectrin/band 3 ratio, which correlated with the normocytic morphology. An abnormal Sp peptide at 41 kD suggested the presence of the LELY mutation. Sequencing of the patient's Sp gene revealed heterozygosity for a novel mutation in exon 2, codon 34: CGG→CCG (Arg>Pro) and heterozygosity for LELY. Mutations were also present in the patient's brother and daughter who have HE, while another son, who had Arg34Pro, but not LELY, had repeatedly confirmed normal morphology.

Ongoing clinical, Sp peptide, DNA and quantitative real time PCR mRNA studies of this extended family reveal a complex interaction of the codon 34: G>C mutation with LELY and levels of Sp allele transcripts. A new method for novel quantitative real time PCR based on a unique primer design was used to determining different levels of transcripts of Sp alleles for a novel mutation in exon 2, codon 34: CGG→CCG (Arg>Pro). Primers were designed in accordance with the disclosed invention, including a mismatch in the −1 position, and a locked nucleic acid nucleoside at the −2 position of the allele-specific primers. Table 1 shows the primer sequences used for allele frequency determination in these experiments.

Total RNA was isolated from peripheral blood granulocytes, platelets and reticulocytes. Real time AS-PCR was performed on an Applied Biosystems 7500 Sequence Detection System (Applied Biosystems, Foster City, Calif., USA). cDNA templates for real time AS-PCR were prepared by the reverse transcriptase PCR from total cellular RNA using 50 ng of mRNA and SuperScript III First-Strand Synthesis SuperMix for qRT-PCR (Invitrogen). Typical reactions (15 ul) consisted of 1× TaqMan Universal PCR master mix (Applied Biosystems); 300 nM universal forward and allele-specific reversed primers; 125 nM FAM-labeled Sp-MGBNFQ probe (Applied Biosystems), (Shown in Table 1); and 2 µl of cDNA. Allele-specific primers were designed using the software program Oligo 6.7 (Molecular Biology Insights, INC., Cascade, Colo., USA) and synthesized by IDT (Integrated Technologies, Coralville, Iowa, USA). Table 1 shows allele frequency results obtained in this study.

TABLE 9

Primer and Probe sequences used for Quantitation of a novel CGG -> CCG mutation in exon 2, codon 34 of the Spectrin gene.

| Primer/Probe | Sequence 5' to 3' |
|---|---|
| FAM-AS-SP-MGB | 6FAM-CACTTCCTGACGCCTC-MGBNFQ (SEQ ID NO: 45) |
| cSP-F | GAAACCGTTGTGGAGAGCAGT (SEQ ID NO: 46) |
| cSP-LNA-G-R | CGCTCCTTGAAACTTTGATAgG (SEQ ID NO: 47) |
| cSP-LNA-C-R | CGCTCCTTGAAACTTTGATAgC (SEQ ID NO: 48) |

TABLE 10

Comparison of G-allele and C-allele frequency in Sp gene in reticulocytes in a Family of Northern European Descent

| Patient number | Hetero/homozygote for novel mutation | G-allele (%) | C-allele (%) |
|---|---|---|---|
| PSp 1 | Heterozygote | 28 | 72 |
| PSp 2 | Heterozygote | 18 | 82 |
| PSp 3 | Heterozygote | 30 | 70 |
| PSp 4 | Homozygote | 100 | 0 |
| PSp 5 | Homozygote | 100 | 0 |

REFERENCES

1. Skoda, R., and Prchal, J. T. 2005. Chronic myeloproliferative disorders—introduction. *Semin Hematol* 42:181-183.
2. Baxter, E. J., Scott, L. M., Campbell, P. J., East, C., Fourouclas, N., Swanton, S., Vassiliou, G. S., Bench, A. J., Boyd, E. M., Curtin, N., et al. 2005. Acquired mutation of the tyrosine kinase JAK2 in human myeloproliferative disorders. *Lancet* 365:1054-1061.
3. James, C., Ugo, V., Le Couedic, J. P., Staerk, J., Delhommeau, F., Lacout, C., Garcon, L., Raslova, H., Berger, R., Bennaceur-Griscelli, A., et al. 2005. A unique clonal JAK2 mutation leading to constitutive signalling causes polycythaemia vera. *Nature* 434:1144-1148.
4. Kralovics, R., Passamonti, F., Buser, A. S., Teo, S. S., Tiedt, R., Passweg, J. R., Tichelli, A., Cazzola, M., and Skoda, R. C. 2005. A gain-of-function mutation of JAK2 in myeloproliferative disorders. *N Engl J Med* 352:1779-1790.
5. Levine, R. L., Wadleigh, M., Cools, J., Ebert, B. L., Wernig, G., Huntly, B. J., Boggon, T. J., Wlodarska, I., Clark, J. J., Moore, S., et al. 2005. Activating mutation in the tyrosine kinase JAK2 in polycythemia vera, essential thrombocythemia, and myeloid metaplasia with myelofibrosis. *Cancer Cell* 7:387-397.
6. Zhao, R., Xing, S., Li, Z., Fu, X., Li, Q., Krantz, S. B., and Zhao, Z. J. 2005. Identification of an acquired JAK2 mutation in polycythemia vera. *J Biol Chem* 280:22788-22792.
7. Ugo, V., Marzac, C., Teyssandier, I., Larbret, F., Lecluse, Y., Debili, N., Vainchenker, W., and Casadevall, N. 2004. Multiple signaling pathways are involved in erythropoietin-independent differentiation of erythroid progenitors in polycythemia vera. *Exp Hematol* 32:179-187.
8. Lacout, C., Pisani, D. F., Tulliez, M., Moreau Gachelin, F., Vainchenker, W., and Villeval, J. L. 2006. JAK2V617F expression in murine hematopoietic cells leads to MPD mimicking human PV with secondary myelofibrosis. *Blood*.
9. Kralovics, R., Guan, Y., and Prchal, J. T. 2002. Acquired uniparental disomy of chromosome 9p is a frequent stem cell defect in polycythemia vera. *Exp Hematol* 30:229-236.
10. Kralovics, R., Stockton, D. W., and Prchal, J. T. 2003. Clonal hematopoiesis in familial polycythemia vera suggests the involvement of multiple mutational events in the early pathogenesis of the disease. *Blood* 102:3793-3796.
11. Bellanne-Chantelot; C., Chaumarel, I., Labopin, M., Bellanger, F., Barbu, V., De Toma, C., Delhommeau, F., Casadevall, N., Vainchenker, W., Thomas, G., et al. 2006. Genetic and clinical implications of the Val617Phe JAK2 mutation in 72 families with myeloproliferative disorders. *Blood* 108:346-352.
12. Germer, S., Holland, M. J., and Higuchi, R. 2000. High-throughput SNP allele-frequency determination in pooled DNA samples by kinetic PCR. *Genome Res* 10:258-266.
13. Jelinek, J., and Prchal, J. T. 2004. Oxygen-dependent regulation of erythropoiesis. *Methods Enzymol* 381:201-210.
14. Newton, C. R., Graham, A., Heptinstall, L. E., Powell, S. J., Summers, C., Kalsheker, N., Smith, J. C., and Markham, A. F. 1989. Analysis of any point mutation in DNA. The amplification refractory mutation system (ARMS). *Nucleic Acids Res* 17:2503-2516.
15. Petersen, M., Nielsen, C. B., Nielsen, K. E., Jensen, G. A., Bondensgaard, K., Singh, S. K., Rajwanshi, V. K., Koshkin, A. A., Dahl, B. M., Wengel, J., et al. 2000. The conformations of locked nucleic acids (LNA). *J Mol Recognit* 13:44-53.
16. Jelinek, J., Oki, Y., Gharibyan, V., Bueso-Ramos, C., Prchal, J. T., Verstovsek, S., Beran, M., Estey, E., Kantarjian, H. M., and Issa, J. P. 2005. JAK2 mutation 1849G>T is rare in acute leukemias but can be found in CMML, Philadelphia chromosome-negative CML, and megakaryocytic leukemia. *Blood* 106:3370-3373.
17. Ahmadian, A., Gharizadeh, B., O'Meara, D., Odeberg, J., and Lundeberg, J. 2001. Genotyping by apyrase-mediated allele-specific extension. *Nucleic Acids Res* 29:E121.
18. Bottema, C. D., and Sommer, S. S. 1993. PCR amplification of specific alleles: rapid detection of known mutations and polymorphisms. *Mutat Res* 288:93-102.
19. Kaltenbock, B., and Schneider, R. 1998. Differential amplification kinetics for point mutation analysis by PCR. *Biotechniques* 24:202-204, 206.
20. Latorra, D., Campbell, K., Wolter, A., and Hurley, J. M. 2003. Enhanced allele-specific PCR discrimination in SNP genotyping using 3' locked nucleic acid (LNA) primers. *Hum Mutat* 22:79-85.
21. Liu, E., Jelinek, J., Pastore, Y. D., Guan, Y., Prchal, J. F., and Prchal, J. T. 2003. Discrimination of polycythemias and thrombocytoses by novel, simple, accurate clonality assays and comparison with PRV-1 expression and BFU-E response to erythropoietin. *Blood* 101:3294-3301.
22. Prchal, J. F., and Axelrad, A. A. 1974. Letter: Bone-marrow responses in polycythemia vera. *N Engl J Med* 290:1382.
23. Prchal, J. F., Adamson, J. W., Steinmann, L., and Fialkow, P. J. 1976. Human erythroid colony formation in vitro: evidence for clonal origin. *J Cell Physiol* 89:489-492.
24. Stopka, T., Zivny, J. H., Stopkova, P., Prchal, J. F., and Prchal, J. T. 1998. Human hematopoietic progenitors express erythropoietin. *Blood* 91:3766-3772.
25. Latorra, D., Arar, K., and Hurley, J. M. 2003. Design considerations and effects of LNA in PCR primers. *Mol Cell Probes* 17:253-259.
26. Scott, L. M., Scott, M. A., Campbell, P. J., and Green, A. R. 2006. Progenitors homozygous for the V617F JAK2 mutation occur in most patients with polycythemia vera, but not essential thrombocythemia. *Blood*.
27. Prchal, J. T. 2005. Polycythemia vera and other primary polycythemias. *Curr Opin Hematol* 12:112-116.

What is claimed is:

1. An oligonucleotide complementary to a target polynucleotide, wherein the oligonucleotide is selected from the group consisting of: SEQ ID No: 9, SEQ ID No: 10, SEQ ID No: 11, SEQ ID No: 12, SEQ ID No: 13, SEQ ID No: 14, SEQ ID No: 15, SEQ ID No: 16, SEQ ID No: 17, or SEQ ID No: 18, wherein the nucleotide at the 3' end of SEQ ID Nos. 9 and 10 is an LNA unit, the nucleotide one position away from the 3' end of SEQ ID Nos. 11 and 12 is an LNA unit, the nucleotide two positions away from the 3' end of SEQ ID Nos. 13 and 14 is an LNA unit, the nucleotide three positions away from the 3' end of SEQ ID Nos. 15 and 16 is an LNA unit, and the nucleotide four positions away from the 3' end of SEQ ID Nos. 17 and 18 is an LNA unit.

2. A method of detecting the presence or absence of a polymorphism in a target polynucleotide in a biological sample, comprising:
   (a) providing an oligonucleotide primer complementary to a target polynucleotide, wherein the oligonucleotide primer comprises an LNA unit, a mismatch nucleobase, and an allele-specific nucleobase corresponding to an allele of the target polynucleotide, wherein the LNA unit is located at a position 0, −1, −2, −3, or −4 from the allele-specific nucleobase, the mismatch nucleobase is located at a position −1 from the allele-specific nucleobase, and the allele-specific nucleobase is located at the 3'-terminal position;
   (b) combining the oligonucleotide primer of (a) and a polymerase enzyme with a biological sample suspected of containing a target polynucleotide under conditions amenable to hybridization of the oligonucleotide primer with the target polynucleotide and synthesis of a primer extension product; and
   (c) detecting the presence or absence of a primer extension product, wherein the presence of a primer extension product is indicative of the presence of an allele corresponding to the allele-specific nucleobase.

3. The method of claim 2, wherein the LNA unit is at the −2 position and the mismatch nucleobase is at the −1 position relative to the allele-specific nucleobase.

4. A method of quantitatively determining the frequency of a first allele and a second allele of a target polynucleotide in a biological sample, comprising:
   (a) amplifying a target polynucleotide in a biological sample using a first oligonucleotide complementary to a first allele of the target polynucleotide, wherein the first oligonucleotide comprises an LNA unit, a mismatch nucleobase, and an allele-specific nucleobase corresponding to a first allele of the target polynucleotide;
   (b) amplifying a target polynucleotide in a biological sample using a second oligonucleotide complementary to a second allele of the target polynucleotide, wherein the second oligonucleotide comprises an LNA unit, a mismatch nucleobase, and an allele-specific nucleobase corresponding to a second allele of the target polynucleotide;
   (c) comparing the cycle threshold for the amplification of (a) and (b); and
   (d) determining the frequency of the first allele and the second allele;
   wherein the LNA unit is located at a position 0, −1, −2, −3, or −4 from the allele-specific nucleobase, the mismatch nucleobase is located at a position −1 from the allele-specific nucleobase, and the allele-specific nucleobase is located at the 3'-terminal position for the first and second oligonucleotides.

5. A method of quantitatively determining the frequency of an allele of a target polynucleotide in a biological sample, comprising:
   (a) amplifying a target polynucleotide in a biological sample using a first oligonucleotide complementary to an allele of the target polynucleotide, wherein the first oligonucleotide comprises an LNA unit, a mismatch nucleobase, and an allele-specific nucleobase corresponding to a first allele of the target polynucleotide;
   (b) calculating the cycle threshold for (a);
   (c) comparing the cycle threshold for (a) with the cycle threshold for amplification of a known standard; and
   (d) determining the frequency of the allele;
   wherein the LNA unit is located at a position 0, −1, −2, −3, or −4 from the allele-specific nucleobase, the mismatch nucleobase is located at a position −1 from the allele-specific nucleobase, and the allele-specific nucleobase is located at the 3'-terminal position for the first oligonucleotide.

6. The method of claim 4, wherein the LNA unit is at the −2 position and the mismatch nucleobase is at the −1 position relative to the allele-specific nucleobase.

7. The method of claim 5, wherein the LNA unit is at the −2 position and the mismatch nucleobase is at the −1 position relative to the allele-specific nucleobase.

8. The oligonucleotide of claim 1 which is selected from SEQ ID NO: 9 and SEQ ID NO: 10, wherein the nucleotide at the 3' end of SEQ ID Nos. 9 and 10 is an LNA unit.

9. The oligonucleotide of claim 1 which is SEQ ID NO: 9, wherein the nucleotide at the 3' end of SEQ ID NO: 9 is an LNA unit.

10. The oligonucleotide of claim 1 which is SEQ ID NO: 10, wherein the nucleotide at the 3' end of SEQ ID NO: 10 is an LNA unit.

11. The oligonucleotide of claim 1 which is selected from SEQ ID NO: 13 and SEQ ID NO: 14, wherein the nucleotide two positions away from the 3' end of SEQ ID Nos. 13 and 14 is an LNA unit.

12. The oligonucleotide of claim 1 which is SEQ ID NO: 13, wherein the nucleotide two positions away from the 3' end of SEQ ID NO: 13 is an LNA unit.

13. The oligonucleotide of claim 1 which is SEQ ID NO: 14, wherein the nucleotide two positions away from the 3' end of SEQ ID NO: 14 is an LNA unit.

14. The oligonucleotide of claim 1 which is selected from SEQ ID NO: 11 and SEQ ID NO: 12, wherein the nucleotide one position away from the 3' end of SEQ ID Nos. 11 and 12 is an LNA unit.

15. The oligonucleotide of claim 1 which is SEQ ID NO: 11, wherein the nucleotide one position away from the 3' end of SEQ ID NO: 11 is an LNA unit.

16. The oligonucleotide of claim 1 which is SEQ ID NO: 12, wherein the nucleotide one position away from the 3' end of SEQ ID NO: 12 is an LNA unit.

17. The oligonucleotide of claim 1 which is selected from SEQ ID NO: 17 and SEQ ID NO: 18, wherein the nucleotide four positions away from the 3' end of SEQ ID Nos. 17 and 18 is an LNA unit.

18. The oligonucleotide of claim 1 which is SEQ ID NO: 17, wherein the nucleotide four positions away from the 3' end of SEQ ID NO: 17 is an LNA unit.

19. The oligonucleotide of claim 1 which is SEQ ID NO: 18, wherein the nucleotide four positions away from the 3' end of SEQ ID NO: 18 is an LNA unit.

* * * * *

UNITED STATES PATENT AND TRADEMARK OFFICE
CERTIFICATE OF CORRECTION

| | | |
|---|---|---|
| PATENT NO. | : 8,580,945 B2 | Page 1 of 1 |
| APPLICATION NO. | : 12/513467 | |
| DATED | : November 12, 2013 | |
| INVENTOR(S) | : Josef T. Prchal et al. | |

It is certified that error appears in the above-identified patent and that said Letters Patent is hereby corrected as shown below:

In the Specification

<u>Column 1, Line 13</u>

Before the "TECHNICAL FIELD OF THE INVENTION" heading, insert the following heading and paragraph:

-- FEDERALLY SPONSORED RESEARCH OR DEVELOPMENT

This invention was made with government support under R01 HL050077 awarded by National Institutes of Health. The government has certain rights in this invention. --

Signed and Sealed this
First Day of September, 2015

Michelle K. Lee
*Director of the United States Patent and Trademark Office*

```
                           SEQUENCE LISTING

<160> NUMBER OF SEQ ID NOS: 48

<210> SEQ ID NO 1
<211> LENGTH: 18
<212> TYPE: DNA
<213> ORGANISM: Homo sapiens

<400> SEQUENCE: 1
cttgctcatc atacttgc                                                        18

<210> SEQ ID NO 2
<211> LENGTH: 25
<212> TYPE: DNA
<213> ORGANISM: Homo sapiens

<400> SEQUENCE: 2
ttatggacaa cagtcaaaca acaat                                                25

<210> SEQ ID NO 3
<211> LENGTH: 25
<212> TYPE: DNA
<213> ORGANISM: Homo sapiens
```

<400> SEQUENCE: 3
tttacttact ctcgtctcca cagac                                    25

<210> SEQ ID NO 4
<211> LENGTH: 25
<212> TYPE: DNA
<213> ORGANISM: Homo sapiens

<400> SEQUENCE: 4
tttacttact ctcgtctcca cagaa                                    25

<210> SEQ ID NO 5
<211> LENGTH: 25
<212> TYPE: DNA
<213> ORGANISM: Homo sapiens

<400> SEQUENCE: 5
tttacttact ctcgtctcca cagac                                    25

<210> SEQ ID NO 6
<211> LENGTH: 25
<212> TYPE: DNA
<213> ORGANISM: Homo sapiens

<400> SEQUENCE: 6
tttacttact ctcgtctcca cagaa                                    25

<210> SEQ ID NO 7
<211> LENGTH: 25
<212> TYPE: DNA
<213> ORGANISM: Homo sapiens

<400> SEQUENCE: 7
tttacttact ctcgtctcca cagtc                                    25

<210> SEQ ID NO 8
<211> LENGTH: 25
<212> TYPE: DNA
<213> ORGANISM: Homo sapiens

<400> SEQUENCE: 8
tttacttact ctcgtctcca cagta                                    25

<210> SEQ ID NO 9
<211> LENGTH: 25
<212> TYPE: DNA
<213> ORGANISM: Homo sapiens

<400> SEQUENCE: 9
tttacttact ctcgtctcca cagtc                                    25

<210> SEQ ID NO 10
<211> LENGTH: 25
<212> TYPE: DNA
<213> ORGANISM: Homo sapiens

<400> SEQUENCE: 10
tttacttact ctcgtctcca cagta                                    25

<210> SEQ ID NO 11
<211> LENGTH: 25
<212> TYPE: DNA
<213> ORGANISM: Homo sapiens

```
<400> SEQUENCE: 11
tttacttact ctcgtctcca cagtc                                              25

<210> SEQ ID NO 12
<211> LENGTH: 25
<212> TYPE: DNA
<213> ORGANISM: Homo sapiens

<400> SEQUENCE: 12
tttacttact ctcgtctcca cagta                                              25

<210> SEQ ID NO 13
<211> LENGTH: 25
<212> TYPE: DNA
<213> ORGANISM: Homo sapiens

<400> SEQUENCE: 13
tttacttact ctcgtctcca cagtc                                              25

<210> SEQ ID NO 14
<211> LENGTH: 25
<212> TYPE: DNA
<213> ORGANISM: Homo sapiens

<400> SEQUENCE: 14
tttacttact ctcgtctcca cagta                                              25

<210> SEQ ID NO 15
<211> LENGTH: 25
<212> TYPE: DNA
<213> ORGANISM: Homo sapiens

<400> SEQUENCE: 15
tttacttact ctcgtctcca cagtc                                              25

<210> SEQ ID NO 16
<211> LENGTH: 25
<212> TYPE: DNA
<213> ORGANISM: Homo sapiens

<400> SEQUENCE: 16
tttacttact ctcgtctcca cagta                                              25

<210> SEQ ID NO 17
<211> LENGTH: 25
<212> TYPE: DNA
<213> ORGANISM: Homo sapiens

<400> SEQUENCE: 17
tttacttact ctcgtctcca cagtc                                              25

<210> SEQ ID NO 18
<211> LENGTH: 25
<212> TYPE: DNA
<213> ORGANISM: Homo sapiens

<400> SEQUENCE: 18
tttacttact ctcgtctcca cagta                                              25

<210> SEQ ID NO 19
<211> LENGTH: 18
<212> TYPE: DNA
<213> ORGANISM: Homo sapiens
```

```
<400> SEQUENCE: 19
gggtcacaga gcgaacca                                              18

<210> SEQ ID NO 20
<211> LENGTH: 19
<212> TYPE: DNA
<213> ORGANISM: Homo sapiens

<400> SEQUENCE: 20
gcctgctgct gctgagctg                                             19

<210> SEQ ID NO 21
<211> LENGTH: 19
<212> TYPE: DNA
<213> ORGANISM: Homo sapiens

<400> SEQUENCE: 21
gcctgctgct gctgagctt                                             19

<210> SEQ ID NO 22
<211> LENGTH: 18
<212> TYPE: DNA
<213> ORGANISM: Homo sapiens

<400> SEQUENCE: 22
gggtcacaga gcgaacca                                              18

<210> SEQ ID NO 23
<211> LENGTH: 18
<212> TYPE: DNA
<213> ORGANISM: Homo sapiens

<400> SEQUENCE: 23
gcctgctgct gctgagct                                              18

<210> SEQ ID NO 24
<211> LENGTH: 18
<212> TYPE: DNA
<213> ORGANISM: Homo sapiens

<400> SEQUENCE: 24
gcctgctgct gctgagca                                              18

<210> SEQ ID NO 25
<211> LENGTH: 17
<212> TYPE: DNA
<213> ORGANISM: Homo sapiens

<400> SEQUENCE: 25
acagtcctgt acggtgg                                               17

<210> SEQ ID NO 26
<211> LENGTH: 23
<212> TYPE: DNA
<213> ORGANISM: Homo sapiens

<400> SEQUENCE: 26
ggagccttgt ctatggatca tgc                                        23

<210> SEQ ID NO 27
<211> LENGTH: 25
<212> TYPE: DNA
<213> ORGANISM: Homo sapiens
```

```
<400> SEQUENCE: 27
cacagaagag cccataggaa tcagg                                          25

<210> SEQ ID NO 28
<211> LENGTH: 25
<212> TYPE: DNA
<213> ORGANISM: Homo sapiens

<400> SEQUENCE: 28
cacagaagag cccataggaa tcagt                                          25

<210> SEQ ID NO 29
<211> LENGTH: 17
<212> TYPE: DNA
<213> ORGANISM: Homo sapiens

<400> SEQUENCE: 29
tgcaggaaca tctgagg                                                   17

<210> SEQ ID NO 30
<211> LENGTH: 23
<212> TYPE: DNA
<213> ORGANISM: Homo sapiens

<400> SEQUENCE: 30
tttatgggtt tggaaacttg cat                                            23

<210> SEQ ID NO 31
<211> LENGTH: 22
<212> TYPE: DNA
<213> ORGANISM: Homo sapiens

<400> SEQUENCE: 31
ctagagtttt gcggttactt gc                                             22

<210> SEQ ID NO 32
<211> LENGTH: 22
<212> TYPE: DNA
<213> ORGANISM: Homo sapiens

<400> SEQUENCE: 32
ctagagtttt gcggttactt gt                                             22

<210> SEQ ID NO 33
<211> LENGTH: 18
<212> TYPE: DNA
<213> ORGANISM: Homo sapiens

<400> SEQUENCE: 33
ccttcctctg agaagtat                                                  18

<210> SEQ ID NO 34
<211> LENGTH: 21
<212> TYPE: DNA
<213> ORGANISM: Homo sapiens

<400> SEQUENCE: 34
cctcgacatg tcttagtgtt t                                              21

<210> SEQ ID NO 35
<211> LENGTH: 22
<212> TYPE: DNA
<213> ORGANISM: Homo sapiens
```

-continued

```
<400> SEQUENCE: 35
tgggatatct tctaaccata gc                                       22

<210> SEQ ID NO 36
<211> LENGTH: 22
<212> TYPE: DNA
<213> ORGANISM: Homo sapiens

<400> SEQUENCE: 36
tgggatatct tctaaccata gt                                       22

<210> SEQ ID NO 37
<211> LENGTH: 14
<212> TYPE: DNA
<213> ORGANISM: Homo sapiens

<400> SEQUENCE: 37
agcgcctcat cctg                                                14

<210> SEQ ID NO 38
<211> LENGTH: 19
<212> TYPE: DNA
<213> ORGANISM: Homo sapiens

<400> SEQUENCE: 38
cagtggggtg aaaatacgc                                           19

<210> SEQ ID NO 39
<211> LENGTH: 17
<212> TYPE: DNA
<213> ORGANISM: Homo sapiens

<400> SEQUENCE: 39
agctccctga cgccttc                                             17

<210> SEQ ID NO 40
<211> LENGTH: 17
<212> TYPE: DNA
<213> ORGANISM: Homo sapiens

<400> SEQUENCE: 40
agctccctga cgccttt                                             17

<210> SEQ ID NO 41
<211> LENGTH: 18
<212> TYPE: DNA
<213> ORGANISM: Homo sapiens

<400> SEQUENCE: 41
taccttctct gaagccag                                            18

<210> SEQ ID NO 42
<211> LENGTH: 20
<212> TYPE: DNA
<213> ORGANISM: Homo sapiens

<400> SEQUENCE: 42
gagactgctg aacacattgc                                          20

<210> SEQ ID NO 43
<211> LENGTH: 20
<212> TYPE: DNA
<213> ORGANISM: Homo sapiens
```

```
<400> SEQUENCE: 43
catctgcttt ctcatgcctc                                                  20

<210> SEQ ID NO 44
<211> LENGTH: 20
<212> TYPE: DNA
<213> ORGANISM: Homo sapiens

<400> SEQUENCE: 44
catctgcttt ctcatgccta                                                  20

<210> SEQ ID NO 45
<211> LENGTH: 16
<212> TYPE: DNA
<213> ORGANISM: Homo sapiens

<400> SEQUENCE: 45
cacttcctga cgcctc                                                      16

<210> SEQ ID NO 46
<211> LENGTH: 21
<212> TYPE: DNA
<213> ORGANISM: Homo sapiens

<400> SEQUENCE: 46
gaaaccgttg tggagagcag t                                                21

<210> SEQ ID NO 47
<211> LENGTH: 22
<212> TYPE: DNA
<213> ORGANISM: Homo sapiens

<400> SEQUENCE: 47
cgctccttga aactttgata gg                                               22

<210> SEQ ID NO 48
<211> LENGTH: 22
<212> TYPE: DNA
<213> ORGANISM: Homo sapiens

<400> SEQUENCE: 48
cgctccttga aactttgata gc                                               22
```